US012660852B2

(12) United States Patent
    Schatz

(10) Patent No.: US 12,660,852 B2
(45) Date of Patent: Jun. 23, 2026

(54) VAPING DEVICE

(71) Applicant: Jared Schatz, Thousand Oaks, CA (US)

(72) Inventor: Jared Schatz, Thousand Oaks, CA (US)

( * ) Notice: Subject to any disclaimer, the term of this patent is extended or adjusted under 35 U.S.C. 154(b) by 363 days.

(21) Appl. No.: 18/236,950

(22) Filed: Aug. 23, 2023

(65) Prior Publication Data

US 2024/0065317 A1 Feb. 29, 2024

Related U.S. Application Data

(60) Provisional application No. 63/400,047, filed on Aug. 23, 2022.

(51) Int. Cl.

| | |
|---|---|
| *A24F 40/30* | (2020.01) |
| *A24F 40/10* | (2020.01) |
| *A24F 40/20* | (2020.01) |
| *A24F 40/42* | (2020.01) |
| *A24F 40/46* | (2020.01) |
| *A24F 40/48* | (2020.01) |
| *A24F 40/60* | (2020.01) |
| *H05B 1/02* | (2006.01) |
| *A61M 15/06* | (2006.01) |

(52) U.S. Cl.
    CPC .............. *A24F 40/30* (2020.01); *A24F 40/10* (2020.01); *A24F 40/20* (2020.01); *A24F 40/42* (2020.01); *A24F 40/46* (2020.01); *A24F 40/48* (2020.01); *A24F 40/60* (2020.01); *H05B 1/0244* (2013.01); *A61M 15/06* (2013.01); *H05B 2203/005* (2013.01)

(58) Field of Classification Search
    None
    See application file for complete search history.

(56) References Cited

U.S. PATENT DOCUMENTS

2014/0060556 A1* 3/2014 Liu ......................... A24F 40/42
                                                                131/329

* cited by examiner

*Primary Examiner* — Katherine A Will

(74) *Attorney, Agent, or Firm* — Shalchi Law PC; Ali Shalchi, Esq.

(57) ABSTRACT

A vaping device is provided that enables a user to vape a plurality of substances. The device includes a strain container having at least three isolated strain chambers each chamber configured to hold an individual substance strain in liquid or solid form, a first system having an electrical assembly configured to activate at least three heating agents each corresponding with a strain chamber and configured to vaporize its corresponding strain. The device also includes a second system having an airflow assembly configured to further isolate the strains in liquid form while providing travel pathways for the vapors, and a conductive housing for components in the first and second systems. The device allows the isolated strains to be vaped individually or in any combination simultaneously, with the second system configured to consolidate the combined vapors into a single airflow to be vaped, where the combination vaping produces at least six strains.

19 Claims, 21 Drawing Sheets

100

100

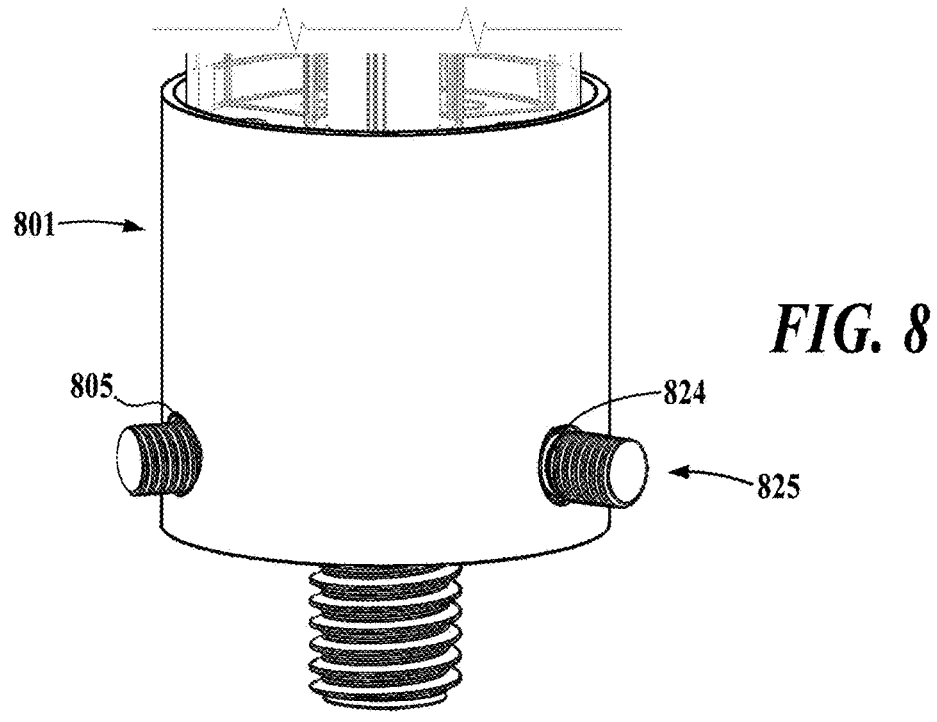
FIG. 8
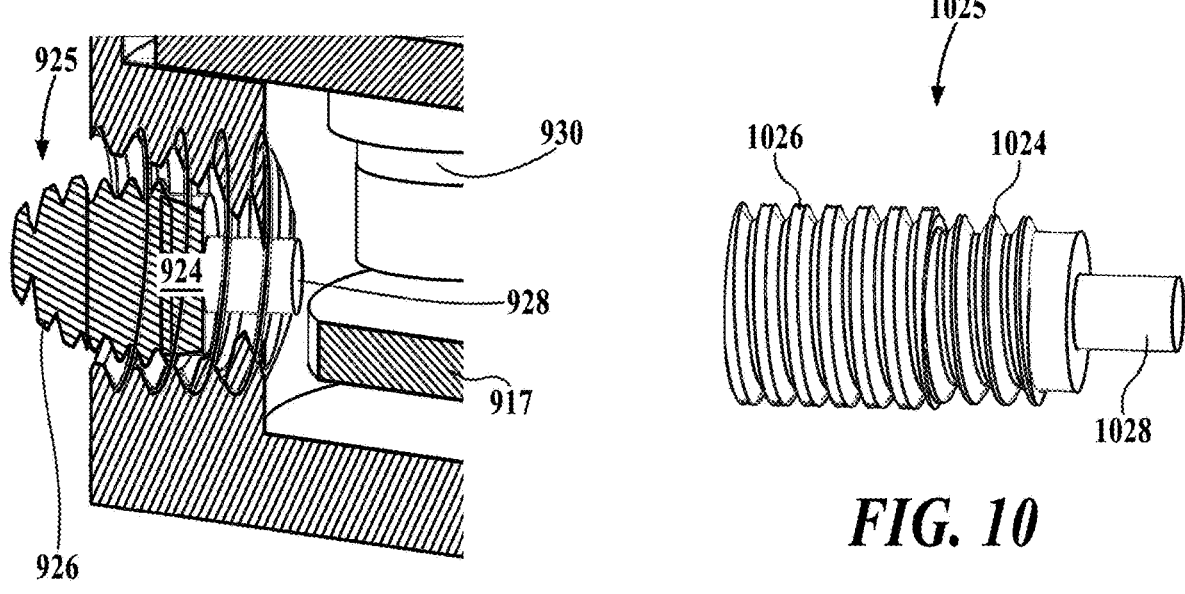
FIG. 9
FIG. 10

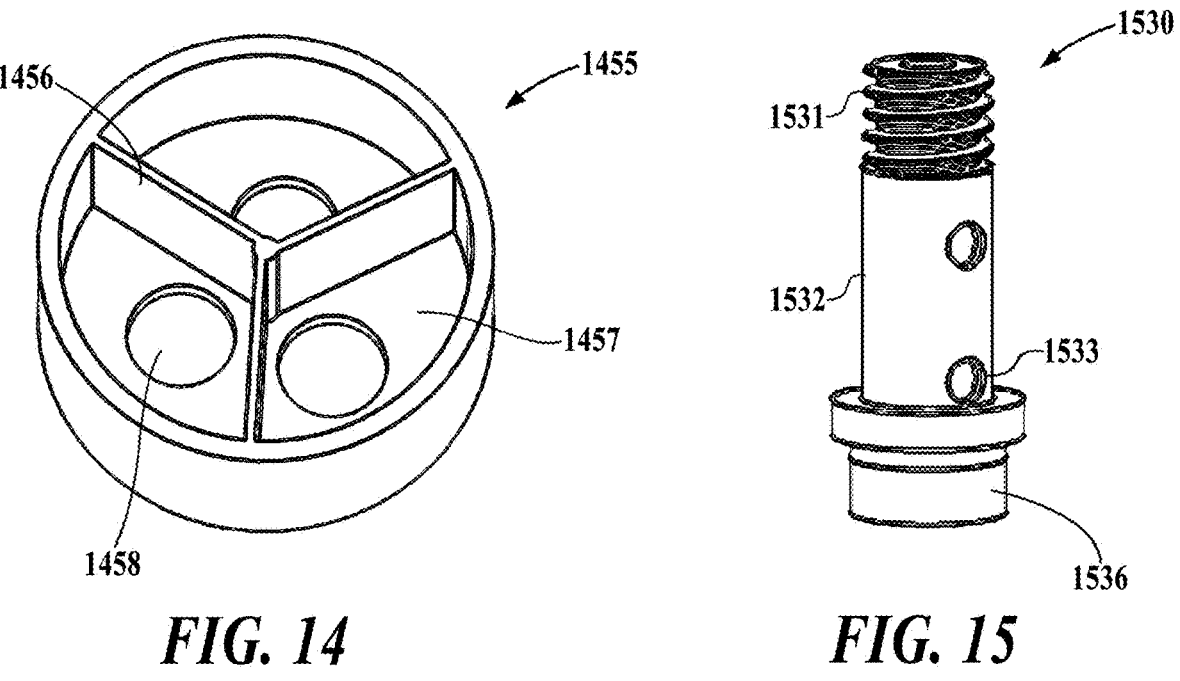
FIG. 14
FIG. 15
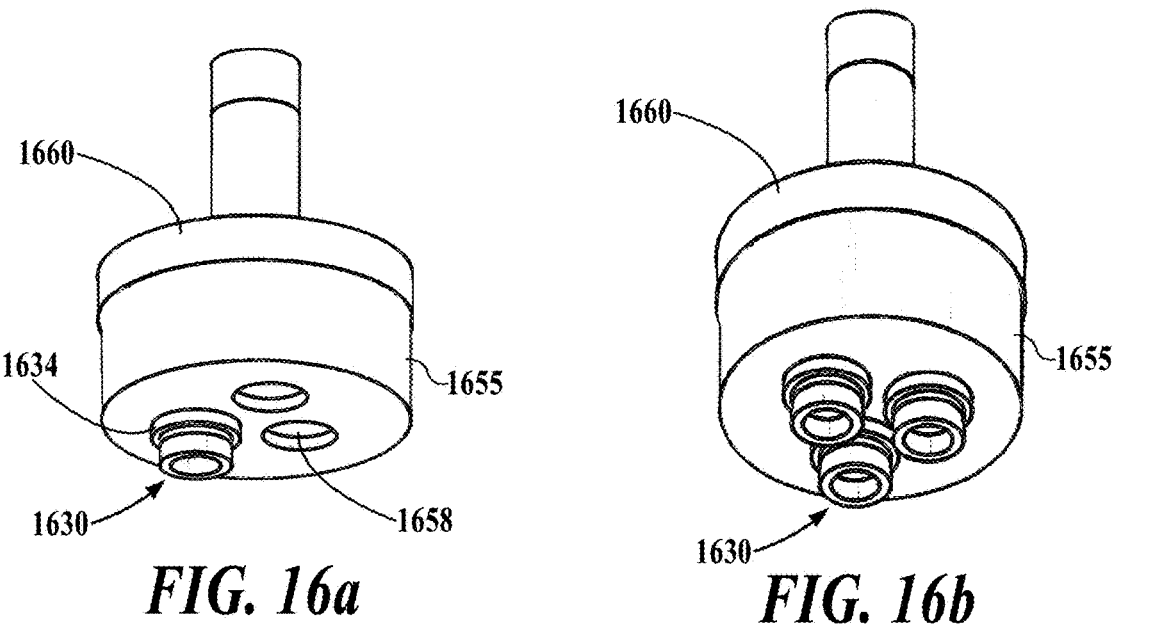
FIG. 16a
FIG. 16b

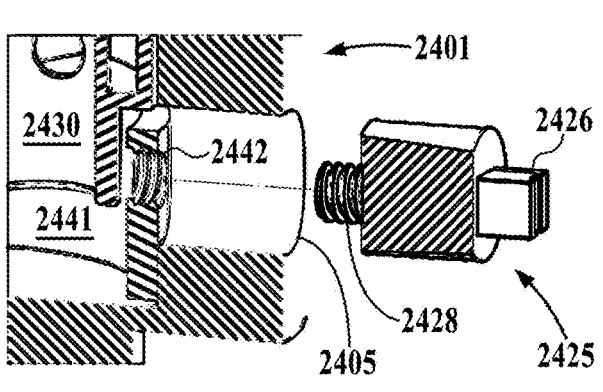
FIG. 24
FIG. 25
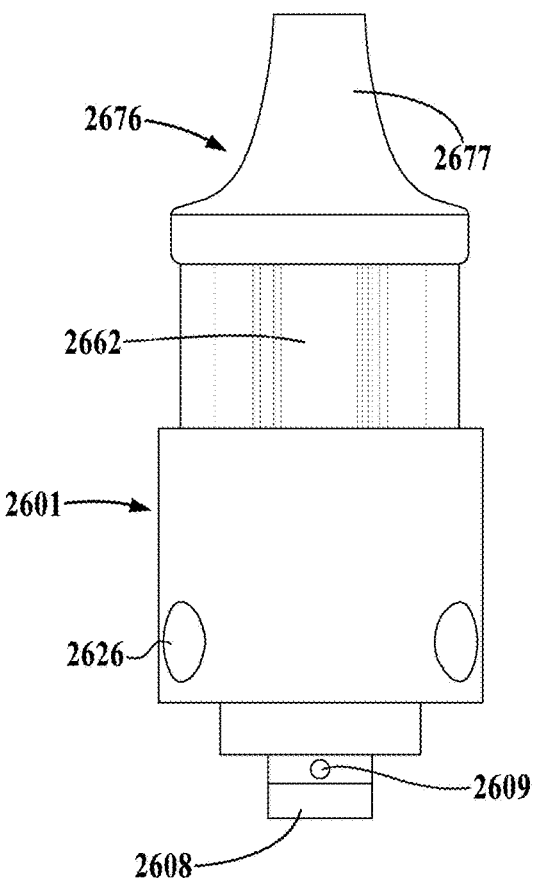
FIG. 26

VAPING DEVICE

RELATED U.S. APPLICATION DATA

This application claims priority to Provisional Application No. 63/400,047, filed Aug. 23, 2022.

FIELD OF THE INVENTION

This disclosure relates to the field of vaping or vaporizer devices.

BACKGROUND

The medical use of cannabis and its constituent cannabinoids, such as tetrahydrocannabinol (THC) and cannabidiol (CBD), includes the treatment of patients suffering from nausea, pain, muscle spasticity, and/or appetite loss. Medicinal cannabis can be administered using a variety of methods, including vaporizing the dried buds of the cannabis plant. Standard THC vaping devices come with about a gram of wax. When smoking wax, THC tolerance is only high for whichever strain a user has been consuming, and there are thousands of strains. Tolerance for the same gram of wax keeps building and building the more the pen is used. When a user first buys a wax pen, two doses may induce a desired bodily response, two days later it may take four doses, in six days it could be 5-7 doses. This not only makes the wax burn extremely hot and expedite the pace of wax burn exponentially each day to achieve the same THC response, it also lowers user tolerance to other strains. This is why many users enjoy other users' THC pens—because their tolerance isn't accustomed to the new strain, thus the individual experiences a much stronger response with fewer doses. The user may believe this is due to the quality of the product, but in reality, their body is simply reacting to a strain that they are not used to. The same effect holds true when it comes to the different types of Cannabis (separated into indica, sativa, or hybrid); a user's body responds to each of these differently. The more of a strain that is introduced, and the more combinations between the three strains, the more THC tolerance can be delayed. Thus, if a user smokes sativa in the morning and indica at night, the THC response is much better, and different. Being able to decide between sativa, indica, hybrid, or a mixture, will allow the body to react in a different way, having a slightly different, better THC response each time. Thus, there is a need in the art for a novel and accessible personal device for simultaneously consuming any of a plurality of THC strains, and combination thereof.

SUMMARY

A vaping device is provided that enables a user to simultaneously vape a plurality of substance strains. In accordance with one embodiment, the device comprises a strain container further comprising an outer cylinder, an inner cylinder, and at least three isolated strain chambers positioned between the outer and inner cylinders, each chamber configured to hold an individual strain as a solid wax. The device also includes a first system including an electrical assembly, that further comprises a prime conductor having a battery contactor, at least three substance activators, each further comprising a secondary conductor and user-controlled portion, at least three tertiary conductors, each further comprising a conductive coil, a tertiary contact, and a hollow body, the hollow body having a threaded top opening and at least one side opening, the hollow body housing the coil, the coil serving as a heating agent, and an insulation system. The electrical assembly is configured to melt the solid wax, the melted wax being vaporized within each hollow body of a tertiary conductor. The device further includes a second system including an airflow assembly that comprises a melted wax holder having at least three bottom openings, at least three larger opposing top openings, and at least three separative walls, the walls forming at least three compartments for receiving melted wax. The device also comprises an airflow consolidator having a consolidated airway and a base portion, the consolidated airway having a threaded top opening, the base portion having at least three threaded base holes and at least three melted wax pathways, the threaded base holes running partially through the base portion, the melted wax pathways running fully through the base portion, each pathway leading from a strain chamber to a wax holder compartment, the inner cylinder of the strain container receiving the consolidated airway. The device also includes an airflow release cap having a threaded cap pathway, wherein the airflow assembly is configured to isolate the melted wax. A supportive housing for components in the first and second systems, the supportive housing further comprising a thick first wall, a thin second wall, an interior floor, and an internal port, the thick wall having at least three openings running through it, both first and second walls each having a circumferential interior surface, the interior surface of the thick first wall extending orthogonally away from the interior floor and terminating in an interior ledge, the interior surface of the thin wall extending orthogonally away from said ledge, the internal port having an exterior with standard threading for accepting a battery, and wherein the substance activators are installed through the supportive housing openings, wherein the insulation system prevents conductive contact between the electrical assembly and the supportive housing, wherein each tertiary conductor corresponds with a strain chamber, a threaded base hole, a melted wax pathway, a melted wax holder compartment and bottom opening, and a secondary conductor, wherein the internal port receives the prime conductor, a connected battery providing electrical current to the prime, secondary, and tertiary conductors via the battery contactor, wherein each paired secondary and tertiary conductor are configured to form an isolated electrical circuit with the prime conductor, the user-controlled portions being manipulatable to close and open each circuit, wherein a closed circuit results in the vaporization of only the corresponding strain, wherein the isolated strains can be vaped individually or in any combination simultaneously, the second system configured to consolidate the combined vapors into a single airflow to be vaped, and wherein the combination vaping produces at least six strains.

In one aspect of the vaping device, the tertiary conductors each have a circumferential lower protrusion and run through the melted wax holder's bottom openings to connect with the airflow consolidator's base holes via the threaded portions, said connection mating components of the airflow assembly together in a secure manner and preventing wax migration into or out of the assembly, the tertiary conductors' lower protrusions each having a diameter exceeding that of each of the melted wax holder's bottom openings, the airflow consolidator's base portion covering and sealing the melted wax holder's top openings, the side opening(s) of each tertiary conductor being isolated with the melted wax in the corresponding melted wax holder compartment, wherein each conductive coil generates heat when its electrical circuit is closed, the heat melting and vaporizing only the wax in the corresponding strain chamber, the melted wax migrating therefrom through only the corresponding melted wax pathway into and being further isolated by only the corresponding melted wax compartment, the melted wax migrating therefrom into only the corresponding tertiary conductor via its side opening(s), the generated vapor traveling through only the corresponding tertiary conductor via its hollow body and exiting out of its top threaded opening, the vapor further traveling into the base portion of the airflow consolidator, therefrom traveling into and through the consolidated airway and finally exiting from the airflow release cap.

In another aspect, the prime and secondary conductors are movable, wherein the prime conductor further comprises a main hot plate, wherein a closed electrical circuit is formed by positioning the main hot plate into conductive contact with a substance activator that has been manipulated by the user to be in conductive contact with its corresponding tertiary conductor, wherein battery installation pushes the prime conductor so that the main hot plate is positioned into said conductive contact, wherein the interior housing ledge supports the airflow assembly and makes contact with the melted wax holder, wherein the strain container's strain chambers are each formed by at least two strain dividers, and wherein the substance activators include active substance indicators configured to visually inform the user that an electrical circuit has been opened or closed, each active substance indicator having a distinct coloration.

In a further aspect, the prime and secondary conductors are non-movable, wherein the secondary and tertiary conductors are in fixed conductive contact, and wherein the thick first wall of the housing supports the airflow assembly via the interior housing ledge. In another aspect, the coils extend from each tertiary conductor and join to form a portion of the prime conductor, the joined coils conductively covered with a coil restraint, wherein the insulation system further comprises an insulative support frame, a coil restraint insulator, and an insulative battery contact support, the insulative support frame positioned upon the interior housing floor and circumferentially contacting the interior surface of the thick first wall, the support frame having at least three holes running through it to receive the secondary conductors, and wherein the interior housing ledge makes contact with the base portion of the airflow consolidator.

In another aspect, the user-controlled portions are a turnable knob-style, a conductive portion of the user-controlled portion making contact with the supportive housing to close the corresponding electrical circuit when the knob is fully turned toward the housing. In a further aspect, the user-controlled portions are dual-state pushbuttons, the substance activator further comprising an external intermediary conductor in fixed conductive contact with the supportive housing, the substance activator configured to close the corresponding circuit once the pushbutton is pressed, and open said circuit when the pushbutton is pressed again.

In another aspect, the pushbuttons include rubber coverings, each rubber covering having a distinct visual indicator via coloration or LED light, and wherein the pressed pushbutton conductively links the secondary conductor, intermediary conductor, and housing, the electrical current returning to the battery via the housing. In yet another aspect, the vaping device includes a microchip to provide a programmed means for vaping at least seven strains, and wherein the user-controlled portions are enhanced with LED lights.

In another embodiment, a vaping device that enables a user to simultaneously vape a plurality of substances, comprises a strain container further comprising at least three isolated strain chambers, each chamber configured to hold an individual strain of a substance in liquid or solid form, a first system including an electrical assembly, the electrical assembly configured to activate at least three heating agents, each heating agent corresponding with a strain chamber, each heating agent configured to vaporize its corresponding strain, a second system including an airflow assembly, the airflow assembly configured to further isolate the strains in liquid form while providing pathways of travel for the vapors, a conductive housing for components in the first and second systems, and wherein the isolated strains can be vaped individually or in any combination simultaneously, the second system configured to consolidate the combined vapors into a single airflow to be vaped, and wherein the combination vaping produces at least six strains.

In one aspect, the strain container further comprises an outer cylinder and an inner cylinder, the strain chambers positioned between the cylinders, wherein the electrical assembly further comprises a prime conductor, at least three substance activators, and at least three tertiary conductors, and wherein the airflow assembly further comprises a liquid substance holder and an airflow consolidator. In another aspect, each substance activator further comprises a secondary conductor and user-controlled portion, and wherein each tertiary conductor further comprises a conductive coil and a hollow body that houses the coil, the coil serving as the heating agent.

In a further aspect, the liquid substance holder further comprises at least three isolated compartments for receiving liquid substance, and wherein the airflow consolidator further comprises a consolidated airway and a base portion, the base portion having at least three base holes and at least three liquid substance pathways, the base holes running partially through the base portion, the liquid substance pathways running fully through the base portion, each pathway leading from a strain chamber to a liquid substance holder compartment, the inner cylinder of the strain container receiving the consolidated airway.

In another aspect, each tertiary conductor corresponds with a strain chamber, a liquid substance pathway, a liquid substance holder compartment, and a secondary conductor, wherein each paired secondary and tertiary conductor are configured to form an isolated electrical circuit with the prime conductor, the user-controlled portions being manipulatable to close and open each circuit, wherein a closed-circuit results in the vaporization of only the corresponding substance.

In a further aspect, the tertiary conductors, liquid substance holder, and airflow consolidator are configured to securely mate together such that liquid substance cannot migrate out of the liquid substance holder, nor can liquid substance enter the holder except through the liquid substance pathways, wherein liquid substance produced from a closed circuit migrates from the corresponding strain chamber to the corresponding liquid substance holder compartment, therefrom migrating into the hollow body of the corresponding tertiary conductor, the hollow body serving as an airway for the vaporized substance, wherein the vapor exits the tertiary conductor and enters the base portion followed by the consolidated airway of the airflow consolidator.

In another aspect, the prime and secondary conductors are non-movable, and wherein the secondary and tertiary conductors are in fixed conductive contact. In a further aspect, the user-controlled portions are a turnable knob-style, a conductive portion of the user-controlled portion making contact with the conductive housing to close the corresponding electrical circuit when the knob is fully turned toward the housing. In another aspect, the user-controlled portions are dual-state pushbuttons, the substance activator configured to close the corresponding circuit once the pushbutton is pressed, and open said circuit when the pushbutton is pressed again. In one aspect, the pushbuttons include coverings, each covering having a distinct visual indicator. In yet another aspect, the vaping device includes a microchip to provide a programmed means for vaping at least seven strains.

BRIEF DESCRIPTION OF THE DRAWINGS

FIG. 8 illustrates a side perspective view of user-adjusted substance activators with visible indicators showing an inactive state in accordance with an embodiment of the present disclosure.

FIG. 9 illustrates a closeup perspective cross-sectional view of outward adjustment of substance activators resulting in an inactive state in accordance with an embodiment of the present disclosure.

FIG. 10 illustrates a closeup side view of a substance activator in accordance with an embodiment of the present disclosure.

FIG. 14 illustrates a top perspective view of a separative melted wax holder in accordance with an embodiment of the present disclosure.

FIG. 15 illustrates a side perspective view of a tertiary conduction airway in accordance with an embodiment of the present disclosure.

FIG. 16*a* illustrates a bottom perspective view of a single tertiary conduction airway installed into a separative melted wax holder in accordance with an embodiment of the present disclosure.

FIG. 16*b* illustrates a bottom perspective view of a nearly complete second system with fully installed components in accordance with an embodiment of the present disclosure.

FIG. 24 illustrates a closeup perspective cross-sectional view of an alternate embodiment of a substance activator being inserted through a housing opening and having a pushbutton style user-controlled portion in accordance with an embodiment of the present disclosure.

FIG. 25 illustrates a side perspective view of an alternate embodiment of a substance activator having a pushbutton style user-controlled portion in accordance with an embodiment of the present disclosure.

FIG. 26 illustrates a front view of an alternate embodiment of a vaping device with thicker housing, covered pushbutton-style user-controlled portions, airflow release cap with modified shape, and modified lower region in accordance with an embodiment of the present disclosure.

DETAILED DESCRIPTION

In the following discussion, numerous specific details are set forth to provide a thorough understanding of the disclosed subject matter. However, those skilled in the art will appreciate that the present disclosed subject matter may be practiced without such specific details. In other instances, well-known elements, processes or techniques have been briefly mentioned and not elaborated on in order not to obscure the disclosed subject matter in unnecessary detail and description. Moreover, specific details and the like may have been omitted inasmuch as such details are not deemed necessary to obtain a complete understanding of the disclosed subject matter, and are considered to be within the understanding of persons having ordinary skill in the relevant art.

Figure 1:
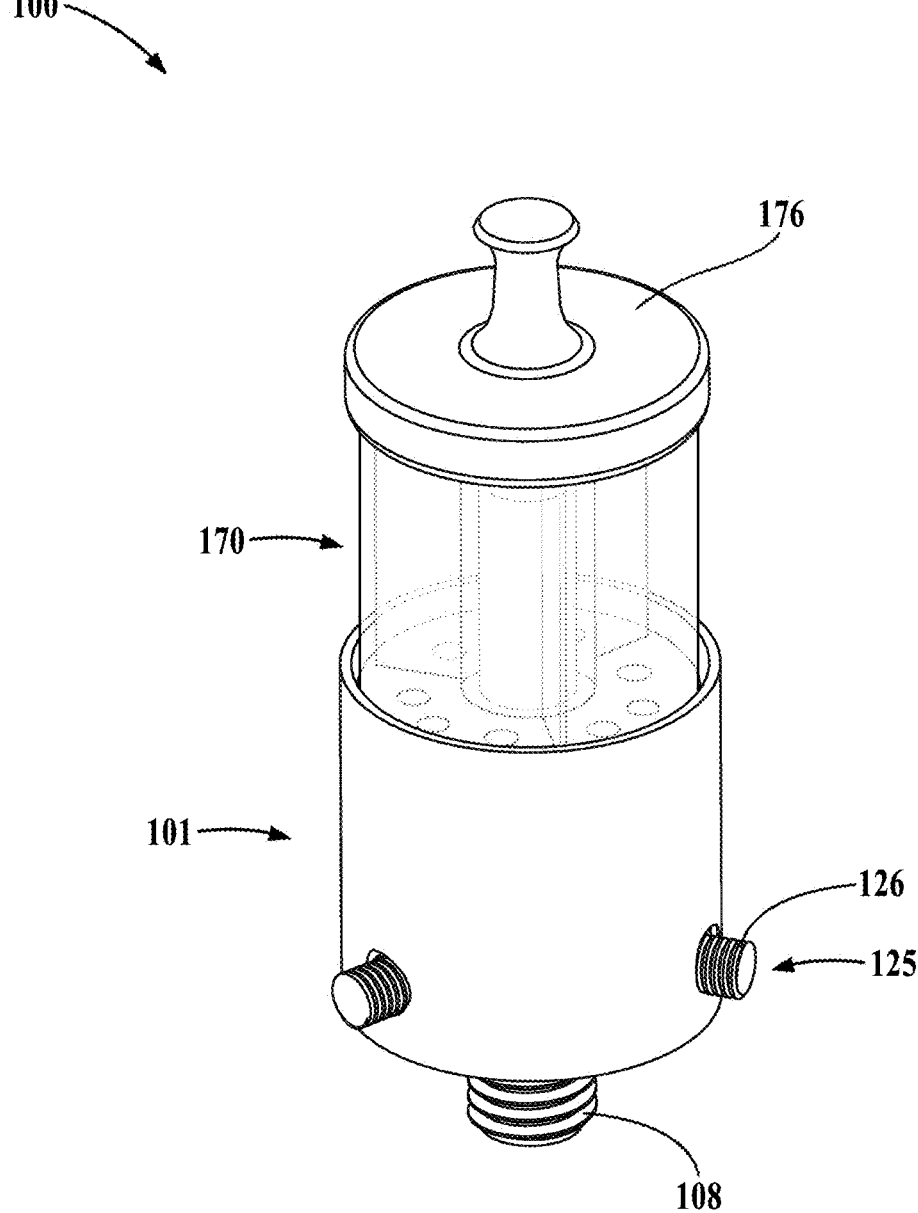
FIG. 1 illustrates a top perspective view of a vaping device in accordance with an embodiment of the present disclosure.

Referring to FIG. 1, a top perspective view shows a vaping device 100 in accordance with an embodiment of the present disclosure. A vaping device 100 comprises a frame or supportive multi-system housing 101 (preferably made of a metal), a strain container 170, a protective airflow release cap 176, and substance activators 125. The housing 101 further comprises an exterior port threading 108, and the substance activators 125 each further comprise user-controlled portions 126. The exemplary embodiment of the present invention shown and described provides a vaping device 100 for vaping nicotine or for serving as a CBD or hemp/THC cartridge, differing from a traditional THC cartridge (which has one coil as a heating agent and contains one strain of a substance) by having a plurality of or at least three coils running through a plurality of or at least three tertiary conduction or conductor airways (see coils 435 of FIG. 4 and tertiary conduction airways 230 of FIG. 2), and at least three different strains. With this combination, a user has the ability to inhale at least six unique strain combinations. In subsequent discussions, the terms "heating agent(s)", "tertiary conduction/conductor airways", and "tertiary conductors" may be used interchangeably, since the end result or goal of tertiary conduction is the heating and melting of a substance, such as a wax. Further, the term "heating agent" may be used interchangeably with the term "coil", since the coil serves as the primary conductive heating agent generating heat, especially in the context of discussions about electrical conductivity. However, it should be noted that the coil(s) has its own separate label, distinct from the higher-level component—tertiary conduction/conductor airway(s), and this distinction will be given attention wherever relevant. Additionally, as the full name of the element suggests, the tertiary conduction airways, like a number of other components discussed below, are dual-use components, each providing an airway as a secondary functional aspect. Other examples may envision the coils alone, with the airways disposed separate from them, or with a substantial portion of the coils extending outside of the airways. Considering most embodiments, a vaping device 100 includes a plurality of or at least three tertiary conductors and substance activators.

A main goal of the present invention is to counteract THC tolerance experienced by a regular user of THC wax, by recognizing the relationship between building a tolerance to a single strain and becoming more sensitive to unused strains. The present invention allows a consumer to use THC at any point of the day without building tolerance by allowing the mixing of strains into various combinations, and also burns wax at a much slower rate than other cartridges. The present invention inevitably saves a user money in the long run, while providing a better response to THC over time; the user will maintain their initial THC response given the same dosage of THC. Thus, the present vaping device is well-suited to every type of user in any scenario. The vaping device 100 includes a plurality of systems that provide several functions. A first system includes an electrical assembly that moves electrical current throughout the vaping device 100 in closed circuits that a user can optionally open by manipulating the substance activators 125. In one example of device usage, a user twists a substance activator 125 in order to control the electrical circuit flow to an individual THC strain, effectively turning it on and off. The source of current for the circuit flow originates from a battery connected at the exterior port threading 108 of the housing 101, the exemplary threading for both the battery and port being industry standard "510" threading. The installed battery makes physical contact with a prime conductor that is in electrical communication with the coils, or tertiary conductors, in a closed circuit. A closed and isolated circuit is made possible only via activity of the substance activators. By manipulating a substance activator 125, a substance-specific secondary conductor (see secondary conductors 228 of FIG. 2), having a structural association with the substance activator, will make or lose contact with a coil or an element having an electrical association with the coil. When there is no direct structural contact or closed electrical communication from the prime conductor to the secondary conductor (when off), no electrical current will pass from the prime conductor to the associated heating agent in the circuit, providing the individual strain with an open circuit. A coil only becomes active and generates heat when its electrical circuit is closed, the heat melting and vaporizing only the wax in a corresponding strain chamber (see strain chamber 1172 of FIG. 11) located above it. A user can choose to have one, two, or three strains activated simultaneously. A closed-circuit results in the vaporization of only a corresponding THC strain, and the isolated THC strains can be vaped individually or in any combination simultaneously. A second system (see second system 450 of FIG. 4) consolidates the combined vapors into a single airflow to be vaped, this combination vaping producing at least six strains. The present device can utilize a coded system, an example of which provides visual feedback via color-coded user-controlled portions 126 found on the substance activators 125. In such an example, each color identifies the strain associated with that particular substance activator 125. By way of example, one color scheme provides the following strain associations: Blue="Baby Yoda" strain, Yellow="Skywalker OG" strain, Purple="Galaxy Demolisher" strain. In this way, the user will not get the various strands confused, and will always know which strain is which. An exemplary vaping device can be manufactured using 3D printing methods, and/or other conventional means known in the art. Some embodiments may provide tertiary conductor airways with a capacitor.

Figures 2, 3:
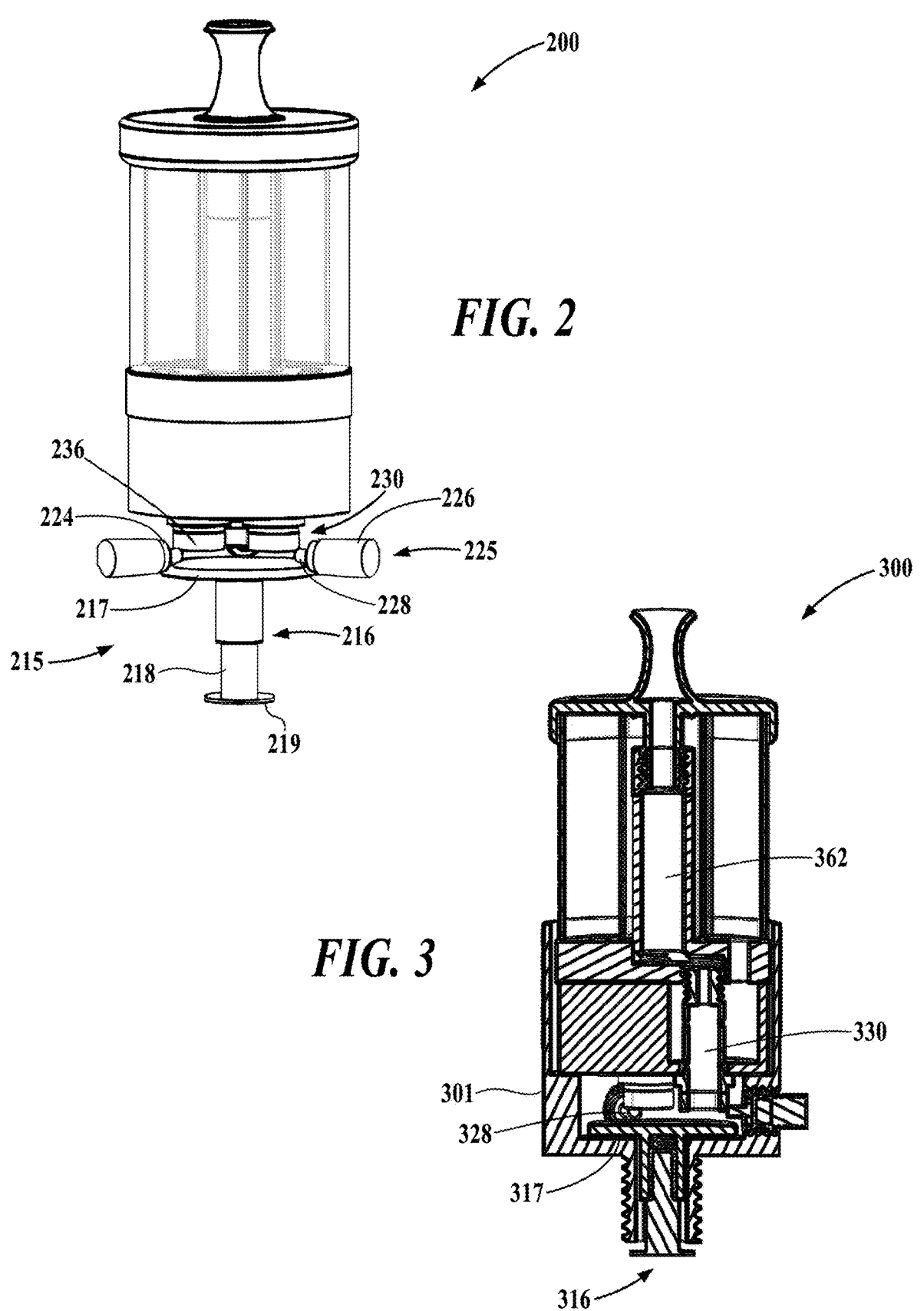
FIG. 2 illustrates a side perspective view of a vaping device in accordance with an embodiment of the present disclosure.
FIG. 3 illustrates a cross-sectional view of a vaping device interior in accordance with an embodiment of the present disclosure.

Referring to FIG. 2, a side perspective view shows a vaping device 200 in accordance with an embodiment of the present disclosure. The device 200 is depicted without the housing depicted in FIG. 1, thus showing major interior components found in one embodiment of an electrical assembly or first system 215. This embodiment exhibits certain color-based design elements. In one example's color scheme, a movable prime conductor 216 comprises plates having a bronze composition and color, including one plate which acts as a main hot plate 217 to the three bronze secondary conductors 228 found on tri-color substance activators 225. The prime conductor further comprises a lower insertable prime pin 218, which makes contact with a battery at one end via a battery contactor 219. At the end opposing the battery contactor 219, the insertable prime pin 218 engages with the main hot plate 217 of the prime conductor 216. Each substance activator 225 is provided with a visual indicator, or active-substance indicator 224, to inform the user when it's ok to stop moving the activator, and is visible when the secondary conductor 228 has been shifted off or away from the main hot plate 217 of the prime conductor as well as off the tertiary conductors 230 and tertiary contacts 236, thereby cutting off the electrical current, or opening the circuit. Each substance activator 225 can be provided with a user-controlled portion 226 of differing color, the different colors identifying each strand. In this embodiment, the three tertiary conduction airways 230 are positioned over the main hot plate 217, in close proximity. Other embodiments may use a conductive metal other than bronze for manufacturing purposes.

Referring to FIG. 3, a cross-sectional view shows an interior of a vaping device 300 in accordance with an embodiment of the present disclosure. A supportive multi-system housing 301 is installed over various lower components found within the device 300. The inner shape of the housing 301 is what holds it in the position shown. The current figure shows a number of critical interior aspects in greater detail. In an exemplary embodiment, components found on the movable prime conductor 316 and secondary conductors 328 consist of a common conductive metal. Proper airflow is a crucial aspect found throughout the structure as a whole. In this exemplary implementation, the optimal airflow allows for all three strains to sit close together yet not mix while using the same consolidated exiting airway 362. The main hot plate 317 is positioned beneath the secondary conductors 328 so that it can rise up and make contact with the secondary conductors when the vaping device 300 as a cartridge is mated with a battery. As long as a secondary conductor 328 is touching a tertiary conductor airway 330, vapor will be produced. There are technically two main systems within this example of a cartridge, the first system being the previously mentioned electrical assembly (see first system 215 of FIG. 2). The electrical assembly melts the isolated solid wax located in the strain container; the melted wax being vaporized within a hollow body of a tertiary conductor 330. In certain contexts, melted wax will also be referred to as a "liquid substance", "oil", or other similar phrase or term.

Figures 4, 5:
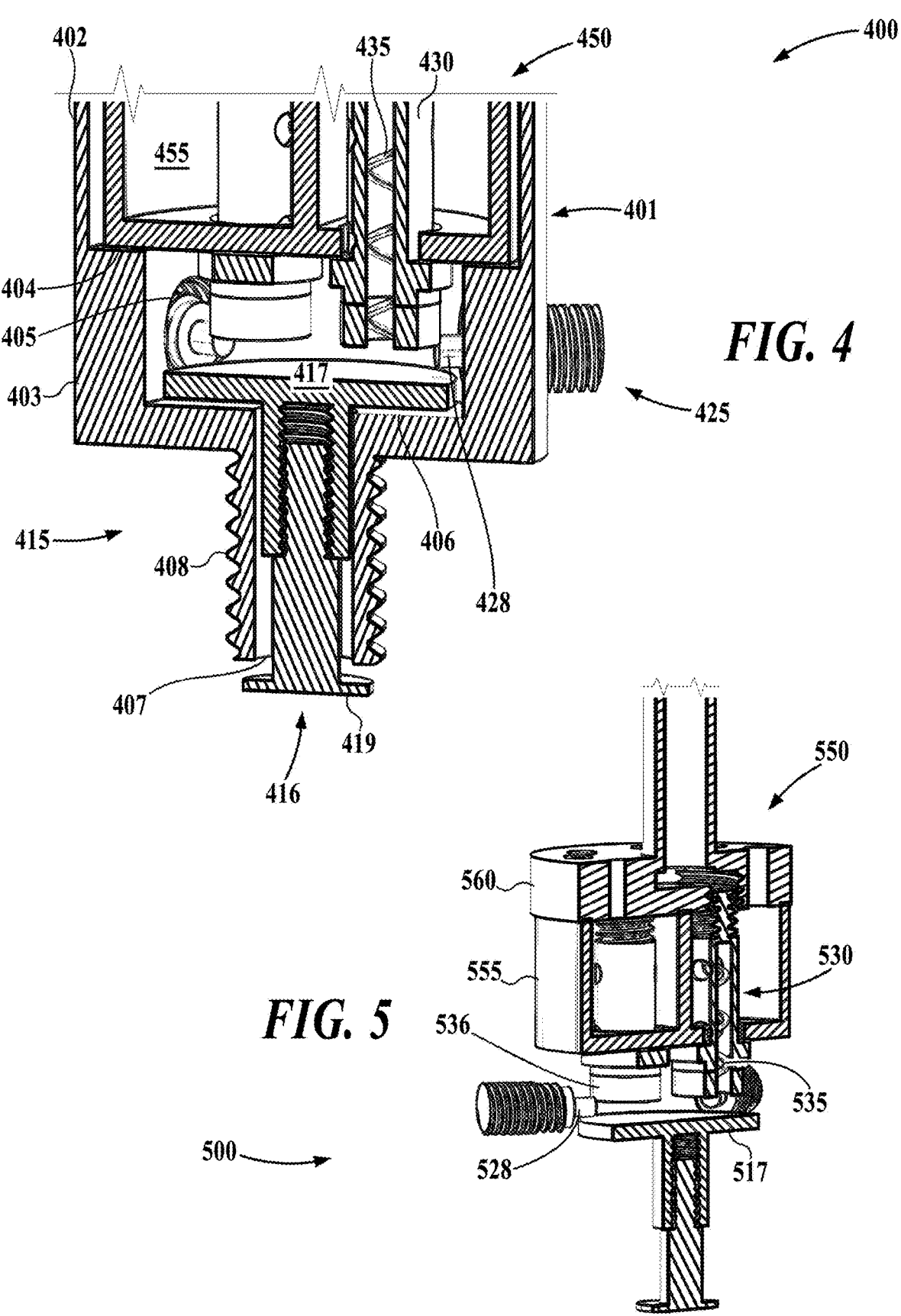
FIG. 4 illustrates a closeup perspective cross-sectional view of lower interior components of a first system in a vaping device in accordance with an embodiment of the present disclosure.
FIG. 5 illustrates a perspective cross-sectional view of interior components of a second system in a vaping device without supportive housing in accordance with an embodiment of the present disclosure.

Referring to FIG. 4, a closeup perspective cross-sectional view shows lower interior components of a first system or electrical conduction assembly 415 in a vaping device 400 in accordance with an embodiment of the present disclosure. A first system 415 comprises electrical circuit components. In an exemplary embodiment, a movable prime conductor 416 comprises a battery contactor 419 and main hot plate 417 that screw together to create a single conductor. An exemplary manufacturing process includes installing the main hot plate 417 into the housing 401 as a first step, followed by the battery contactor 419—which gets screwed into the main hot plate in a second step. The housing 401 has an interior floor 406 onto which the main hot plate 417 is placed. Extending above this floor 406, is an interior ledge 404 for holding a second system, or airflow assembly 450, the ledge forming a top circumferential surface of a thicker lower portion, or thick first circumferential wall 403, such that the top surface of the ledge runs orthogonally to the thick first wall. The airflow assembly 450 thus sits upon the above top circumferential surface in this embodiment, the ledge 404 supporting the assembly and making contact with a separative melted wax holder 455, also referred to as a liquid substance or oil holder. The airflow assembly 450 plays a crucial role in further isolating wax in a melted or liquid/oil form. A thin second wall 402 extends upward from the thick first wall 403. The thick first wall 403 and thin second wall 402 each have a circumferential interior surface, the interior surface of the thick first wall extending orthogonally away from the interior floor 406 and terminating in an interior ledge 404, the interior surface of the thin wall extending orthogonally upward and away from the ledge. In this embodiment, the thin second wall 402 circumferentially surrounds the melted wax holder 455 and base portion (see base portion 1163 of FIG. 11) of an airflow consolidator (see airflow consolidator 560 of FIG. 5). The interior housing floor 406 opens centrally into an internal port 407 extending downward and orthogonally away from the floor, running through the housing interior to terminate at an exterior opening—wherethrough the prime conductor 416 is received. The thick first wall 403 of the housing 401 includes at least three threaded holes or housing openings 405 that accept the substance activators 425. The battery contactor 419 will touch a battery, providing an electrical circuit for the three substance-specific secondary conductors 428; if three substance strains have been simultaneously activated, all three will produce smoke. When the cartridge is not connected to the battery (as seen in the current drawing), gravity will pull the movable prime conductor 416 down, so that the main hot plate 417, is physically separated from the secondary conductors 428. The only way for the main hot plate 417 to touch the secondary conductors 428 and initiate vapor production is to screw the cartridge into the battery, in effect pushing the hot plate upward and forming an electrical connection between secondary conductor 428 and prime conductor 416. The battery used to power the wax vaping device 400 provides a voltage that yields the same amount of smoke whether one tertiary conductor 430 is activated or all three. The small coil 435 within the tertiary conductor 430 can only carry a fixed amount of current no matter the voltage, and because of the device's design, each coil gets the same voltage, regardless of whether one, two, or three secondary conductors 428 are touching the main hot plate 417; the power is not split to divide itself between coils. These structures and activities provide a consistent production of smoke each time, per activated strain. Above and in close proximity to the secondary conductors 428 lie the tertiary conduction airways 430 with copper-contacted coils 435 in an exemplary embodiment. An important aspect of the present invention is that the coil's electrical current is sufficient to produce heat since the coil is substantially mated with an exemplary conductive metal such as copper. As a consequence, contact between a coil 435 (or other structurally associated conductive element) and a strain-specific secondary conductor 428 (if that conductor is touching the main hot plate 417) will create vapor. A further element of such an exemplary embodiment includes cotton, which serves to absorb wax placed in the device 400. Referring back to the lower portion of the prime conductor 416, the diameter of its battery contactor 419 is slightly larger than the above-mentioned exterior opening of the internal port 407, which is a hole running through a lower threaded portion, or exterior port threading 408, of the supportive housing 401 surrounding it and extending away from the housing. This difference in diameters acts as a safety system that prevents the main hot plate 417 from rising too far up, and ensures that an error doesn't occur causing the hot plate to touch the upper tertiary conduction airways 430 instead of the secondary conductors. A crucial aspect of the present invention provides secondary conductors 428 that are physically in contact with the tertiary conductors 430 or coils 435.

Referring to FIG. 5, a perspective cross-sectional view shows interior components of the second system 550 in the vaping device 500 without supportive housing in accordance with an embodiment of the present disclosure. Regarding the tertiary conduction airways 530, a conductive tip of an exemplary coil 535 touches a tertiary contact 536 where the coil terminates, the tertiary contact having copper as an exemplary composition. In one example of manufacturing, the coil 535 and copper are welded together. This ensures that specific, detailed installation isn't necessary later on, since the individual secondary conductor 528 need only touch the tertiary contact 536, or copper portion, instead of touching the coil 535 (the small wire serving as the heating agent) itself. Thus, this aspect of engineering ensures that pinpoint accuracy isn't necessary during subsequent manufacturing stages or regular usage and activation of the cartridge. Additionally, the main hot plate 517 is physically positioned below the secondary conductors 528, this is where physical contact will be made. An exemplary embodiment utilizes cotton for wax absorption. The current drawing also depicts components which provide airflow throughout the system, including a dual-use airflow consolidator 560 lying above and mated with a separative wax/oil holder 555 for receiving melted wax (the phrase "melted wax" is used interchangeably with "oil", since melted wax can just as easily be characterized as an oily substance). Within the wax/oil holder 555 lie the tertiary conduction airways 530. An exemplary composition for the wax/oil holder 555 can be a heat resistant plastic.

Figure 6:
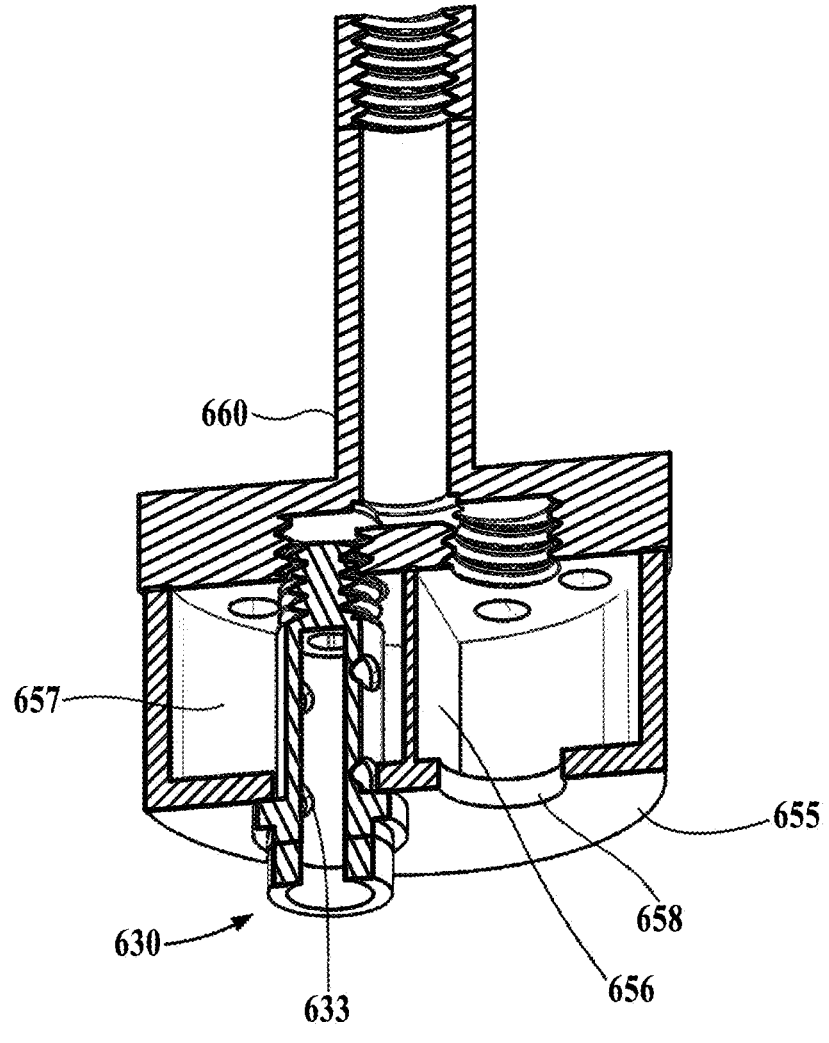
FIG. 6 illustrates a perspective cross-sectional view of installation of tertiary conduction airways in accordance with an embodiment of the present disclosure.

Referring to FIG. 6, a perspective cross-sectional view shows installation of tertiary conduction airways 630 in accordance with an embodiment of the present disclosure. For an exemplary embodiment, this drawing shows what is structurally taking place when screwing the tertiary conduction airways 630 into an airflow consolidator 660. A separative wax/oil holder 655 includes bottom openings 658 which are sealed by the tertiary conduction airways 630. At the same time, airflow within the system is now established and closed off to be airtight. Moreover, sufficient space is maintained for interior components, so that no contact is made between the top of the tertiary conduction airways 630 and a bottom portion of the airflow consolidator 660. This ensures an even and well distributed flow of air. As well, each tertiary conduction airway 630 has at least one side body opening 633 or hole running through it, including primary or lower holes that play an especially crucial role, due to their position. During device usage, the primary lower body openings 633 allow a last bit of wax to drip through and into the tertiary conduction airways 630, ensuring that all wax is converted to vapor, and not wasting any. The wax/oil holder 655 further comprises at least three separative walls 656 that form at least three wax compartments 657 for the incoming wax. In an exemplary embodiment, the separative walls 656 of the wax/oil holder 655 are slightly slanted to increase the flow of wax to the very bottom of the holder.

Figure 7:
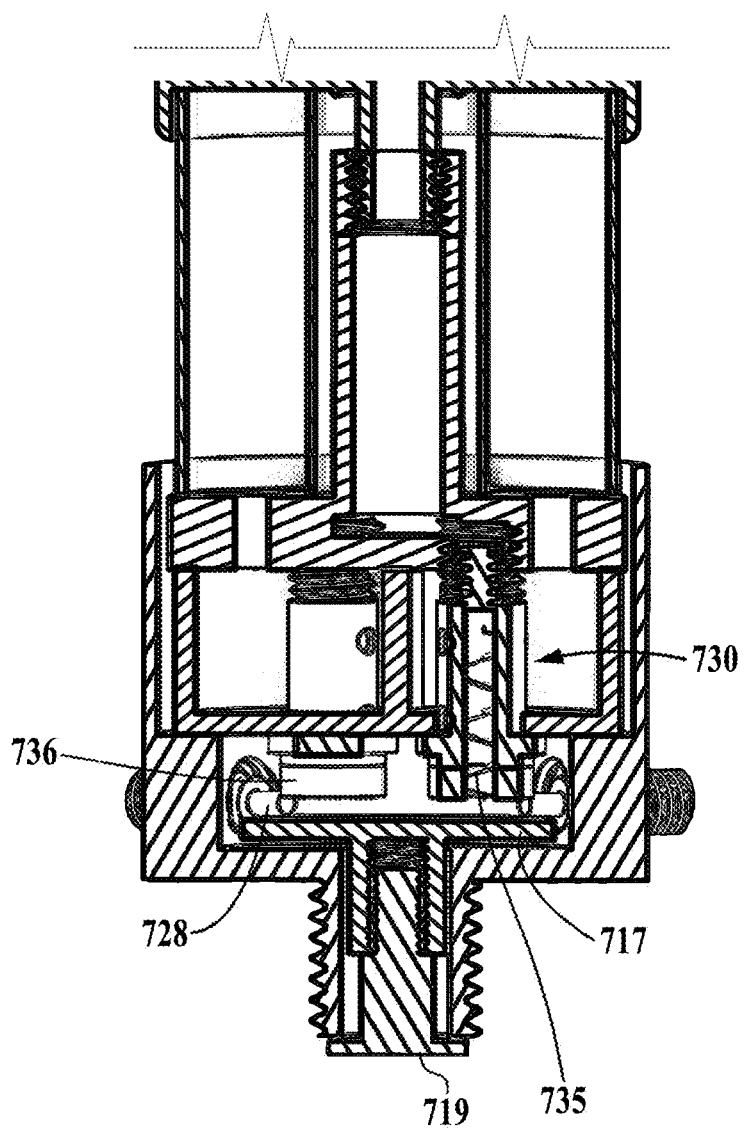
FIG. 7 illustrates a cross-sectional view of an activated vaping device in accordance with an embodiment of the present disclosure.

Referring to FIG. 7, a cross-sectional view shows an activated vaping device 700 in accordance with an embodiment of the present disclosure. Here, the cartridge is active, and the two presently depicted tertiary conductor airways 730 are capable of producing vapor. The main hot plate 717 has moved toward the secondary conductors 728 to establish contact. Not shown in this drawing is the battery, which would be touching the battery contactor 719. The top of the main hot plate 717 is touching secondary conductors 728, which are also touching the tertiary contacts 736 of the coils 735, activating the specific strains associated with each conductor 728.

Referring to FIG. 8, a side perspective view shows user-adjusted substance activators 825 with visible indicators 824 showing an inactive state in accordance with an embodiment of the present disclosure. Active substance indicators 824 on each substance activator extend past the housing openings 805 of the housing 801, and can include a coloration, which lets users know that the substance-specific secondary conductor is out of the way of the hot plate and the associated strain is not active. This prevents the creation of vapor, due to the disconnection of the electrical circuit. In the current embodiment, the hot plate will only activate a THC strain if it touches a secondary conductor while the secondary conductor is touching the tertiary contact of the coil. This highlights a unique benefit of a cartridge that has substance activators 825 that the consumer can control.

Referring to FIG. 9, a closeup perspective cross-sectional view shows outward adjustment of substance activators 925 resulting in an inactive state in accordance with an embodiment of the present disclosure. In this view, the active substance indicator 924 is visible from the outside of the cartridge. In an exemplary usage scenario, the user manipulates or screws the user-controlled portion 926 of the substance activator 925 so that the secondary conductor 928 moves out of the way of the main hot plate 917 and does not connect its copper to the tertiary conductor 930. Since the secondary conductor 928 is disconnected from the hot plate 917, an installed battery can push the hot plate upward, and no contact will be made with the tertiary conduction airway 930, closing the electrical communication to the associated strain. Thus, as shown, upward movement of the main hot plate 917 does not form a complete circuit of electrical communication unless it is physically touching a secondary conductor 928 with contacted tertiary conductor 930.

Referring to FIG. 10, a closeup side view shows a substance activator 1025 in accordance with an embodiment of the present disclosure. In this isolated image of an individual substance activator 1025, the user-controlled portion 1026 indicates a colored area to represent the type of substance or strain associated with it. As well, in an exemplary embodiment, a visible colored active substance indicator 1024 lets the user know when to stop screwing the substance activator 1025 since the secondary conductor 1028 has lost contact with the hot plate at that point. An exemplary composition for both the user-controlled portion 1026 and active substance indicator 1024 is plastic. The secondary conductor 1028 is a smaller end portion of the substance activator 1025 that makes contact with the tertiary contact and thus coil of the tertiary conductor, as well as the main hot plate. An exemplary shape of a secondary conductor 1028 allows it to easily enter through the above-mentioned openings found on the supportive multi-system housing while also allowing the main hot plate to sit immediately below it. Additionally an installed secondary conductor 1028 is well-centered upon the larger structure, maintaining its central position while ensuring its direct entry into the interior region of the cartridge without interference from the rotated user-controlled portion. An exemplary secondary conductor 1028 has a bronze composition. Installing a battery will cause the hot plate to rise upward and touch an active secondary conductor 1028, resulting in its associated substance or strain being activated.

Figure 11:
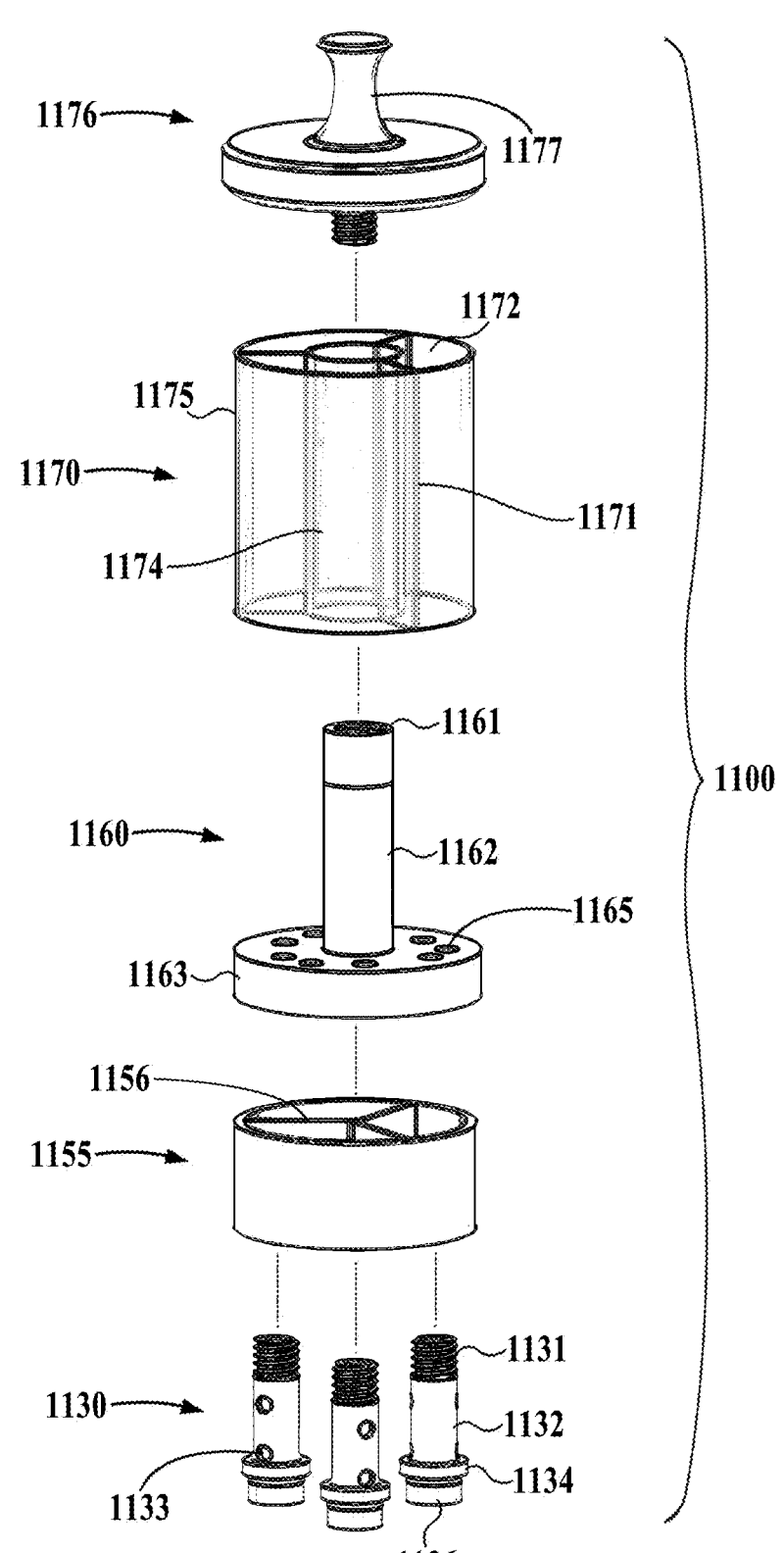
FIG. 11 illustrates an exploded view of components of a vaping device in accordance with an embodiment of the present disclosure.

Referring to FIG. 11, an exploded view shows components of a vaping device 1100 in accordance with an embodiment of the present disclosure. This view includes several pieces necessary for both systems, although highlighting the second system or airflow assembly, apart from the supportive housing holding it all together. Shown in this view are three tertiary conduction airways 1130, each comprising a hollow, cylindrical coil-housing body 1132, tertiary contact 1136, threaded/open top portion 1131, side body openings 1133, a circumferential lower protrusion 1134, cotton (not shown), and conductive coil (not visible in this view, see coil 735 of FIG. 7) that heats up to create vapor. This embodiment of the strain container 1170 comprises two concentric glass or FDA heat-certified plastic cylinders, including an inner cylinder 1174 and an outer cylinder 1175 and three plastic strain dividers 1171 that form strain chambers 1172 for the different strains of solid wax. Considering most embodiments, a strain container 1170 comprises a plurality of or at least three strain chambers 1172 positioned between the inner cylinder 1174 and outer cylinder 1175, the strain chambers each formed by at least two strain dividers 1171. A separative wax/oil holder 1155 has at least three bottom openings (not shown), at least three separative walls 1156, and can be composed of metal or plastic. In the depicted embodiment, the airflow consolidator 1160 comprises a tall hollow stem portion serving as a consolidated airway 1162, and a substantially wider base portion 1163 with nine small holes, or melted wax pathways 1165, also referred to as liquid substance or oil pathways, running fully through the full height of the base portion, along with at least three threaded base holes (see base holes 1364 of FIG. 13a) running partially through the height of the base portion. Considering most embodiments, an airflow consolidator 1160 comprises a plurality of or at least three melted wax pathways 1165. In a complete vaping device, the large threaded base holes continue the flow of air from the tertiary conduction airways 1130 to the consolidated airway 1162, which terminates in a threaded top opening 1161 and consolidates all three separate tertiary conductor airways. A protective airflow release cap 1176, with lower threaded portion of a cap pathway 1177, screws onto the threaded top opening 1161 of the airflow consolidator 1160.

Figure 12A:
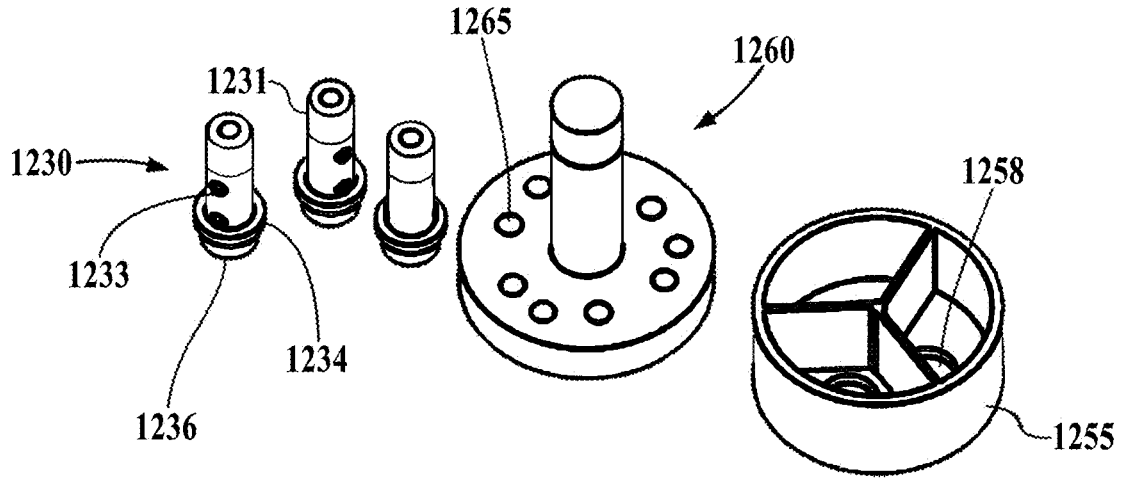
FIG. 12*a* illustrates a top perspective view of components of a second system in a vaping device in accordance with an embodiment of the present disclosure.

Referring to FIG. 12a, a top perspective view shows components of the second system in the vaping device in accordance with an embodiment of the present disclosure. Several pieces necessary for the second main system, or airflow assembly, are shown. This includes three tertiary conduction airways 1230, each with side body openings 1233, cotton (not shown), interior conductive coil (not visible in this view, see coil 735 of FIG. 7), tertiary contact 1236, threaded/open top portion 1231, and circumferential lower protrusion 1234 to fully seal the bottom openings 1258 found on the separative wax/oil holder 1255. Each lower protrusion 1234 has a diameter exceeding that of each bottom opening 1258. The airflow consolidator 1260 is a dual-use component that provides the final path of consolidated air from all three strains and also serves as the roof support for both systems within the housing, to avoid wax leakage. Further, the melted wax pathways 1265 could be viewed as providing the second or third role or function of the airflow consolidator 1260.

Figure 12B:
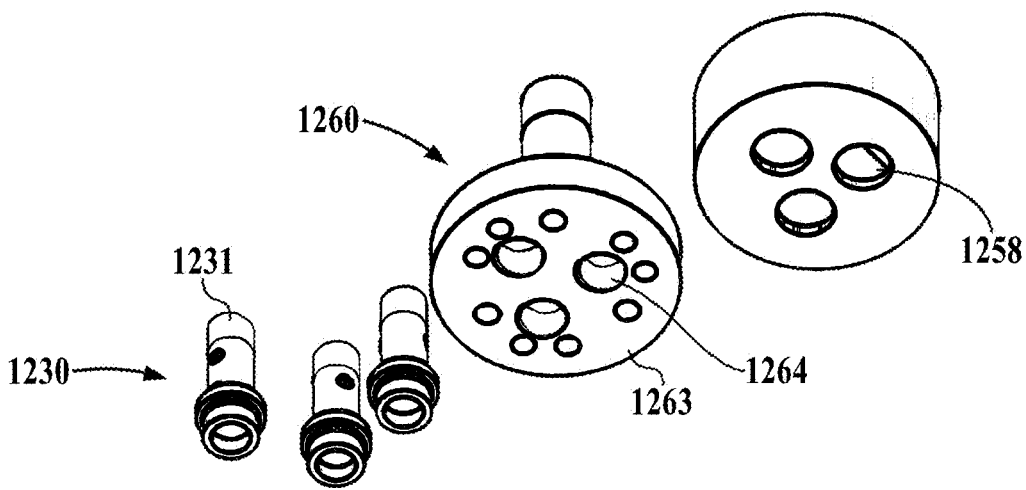
FIG. 12*b* illustrates a bottom perspective view of components of a second system in a vaping device in accordance with an embodiment of the present disclosure.

Referring to FIG. 12b, a bottom perspective view shows components of the second system in the vaping device in accordance with an embodiment of the present disclosure. Again, several pieces necessary for the second main system are shown, from a different perspective. This view shows three threaded base holes 1264 found in the base portion 1263 of the airflow consolidator 1260, at least three base holes being provided in any embodiment. These holes provide the connection points for the tertiary conduction airways 1230—which first pass through the bottom openings 1258 of the wax/oil holder 1255, then are held in place by twisting into threaded base holes 1264 via their threaded top portions 1231. Moreover, this aspect of the manufacturing process not only keeps the tertiary conduction airways 1230 in place but also holds the entire second system together, maintaining its integrity.

Figure 13A:
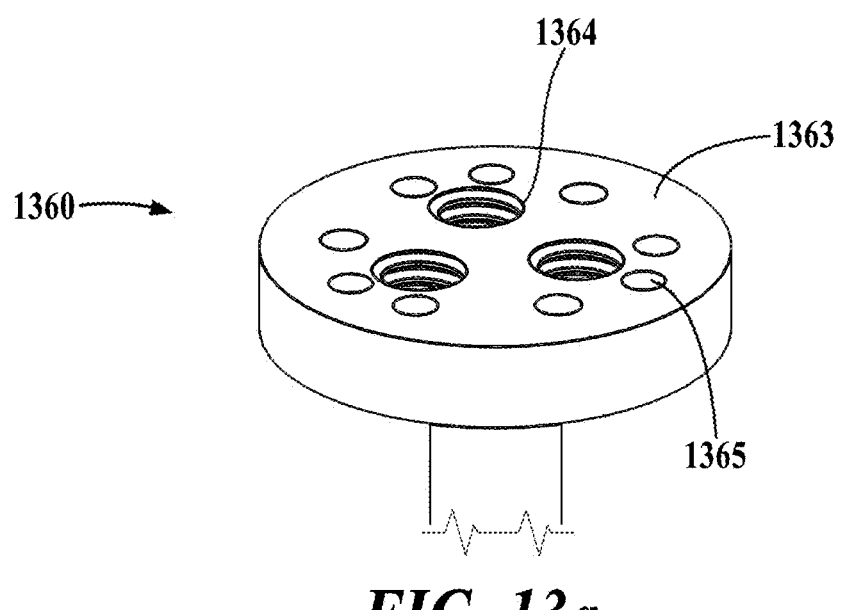
FIG. 13*a* illustrates a bottom perspective view of an airflow consolidator in accordance with an embodiment of the present disclosure.

Referring to FIG. 13a, a bottom perspective view shows an airflow consolidator 1360 in accordance with an embodiment of the present disclosure. The threaded base holes 1364 run just deep enough through the base portion 1363 that the tops of the tertiary conduction airways avoid contact with the roof of the base portion 1363 when installed. This holds the system together while also ensuring that no wax seeps out. As well, the current view of this embodiment highlights the nine small holes or melted wax pathways 1365 running all the way through the base portion 1363. These pathways 1365 allow wax to seep through so that the cotton within can soak it up and be prepared to burn. In this embodiment, the nine small melted wax pathways 1365 are positioned into groups of three, in a circle immediately surrounding the three large threaded holes 1364. The gaps between the groups of three provide a layout onto which the strain dividers (see strain dividers 1171 of FIG. 11) of the glass or plastic strain container can be placed, making alignment easy and simple.

Figure 13B:
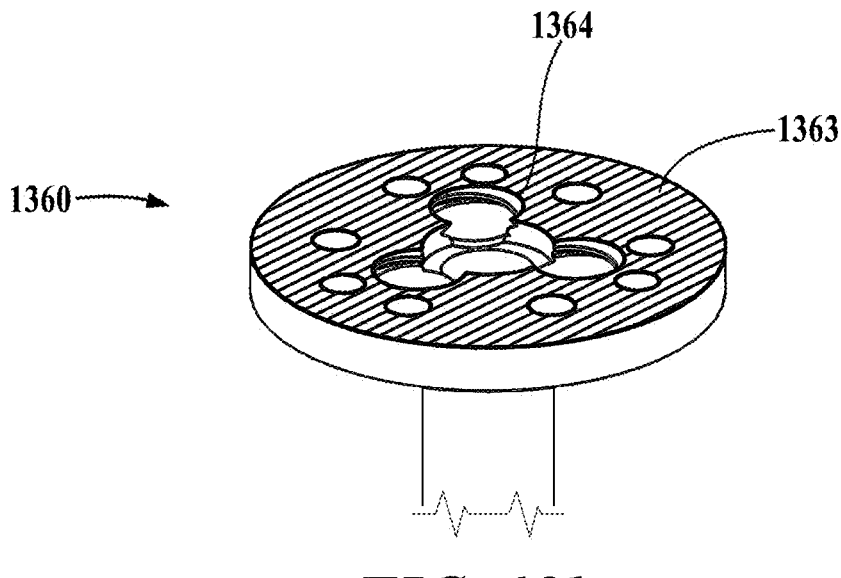
FIG. 13*b* illustrates a bottom perspective cross-sectional view of an airflow consolidator in accordance with an embodiment of the present disclosure.

Referring to FIG. 13b, a bottom perspective cross-sectional view shows an airflow consolidator 1360 in accordance with an embodiment of the present disclosure. This view highlights how the system of airflow is connected and consolidated. The inner surfaces shown are not visible on a finished component. The actual base portion 1363, shown in the previous figure, is taller. Thus, the integrity of airflow is maintained, and immune to clogging issues from wax migration and threaded base holes 1364 of low depth. The threaded top portions of the tertiary conduction airways (see threaded top portions 1231 of FIG. 12b) are long enough to screw in, but not so long that they touch the upper roof of the base portion 1363. A number of components found within the vaping device play two or more roles and have a plurality of functions. For example, the tertiary conduction airways block and seal bottom openings of the separative wax/oil holder (see bottom openings 1258 of FIG. 12b), provide and connect airways, burn wax, and connect components of the second system. Since their primary function includes an electrical association, the tertiary conduction airways are primarily envisioned as being part of the first system (electrical assembly).

Referring to FIG. 14, a top perspective view shows a separative wax/oil holder 1455 in accordance with an embodiment of the present disclosure. The tertiary conduction airways enter through the bottom openings 1458, each exiting one of at least three larger opposing top openings during installation. The purpose of the melted wax holder's design is to create a space to be filled with melted wax or oil to surround the tertiary conduction airways, so that wax can be absorbed while a space is provided to produce vapor. The wax/oil holder 1455 is also designed to separate the three THC strains via the separative walls 1456 which form the wax compartments 1457, such that the compartments accept and hold the melted wax in an isolated fashion. In this way, when a user desires to smoke only one strain, it will be vapor that is 100 percent derived from the desired strain. If a cartridge uses only one coil or heating agent for all strains, then the resulting vapor provides a hybrid of all the strains. The present invention provides three coils within their respective tertiary conduction airways in order to maintain the integrity of each individual THC strain.

Referring to FIG. 15, a side perspective view shows a tertiary conduction airway 1530 in accordance with an embodiment of the present disclosure. The individual conductor airway 1530 has a threaded/open top portion 1531, a hollow and cylindrical coil-housing body 1532, tertiary contact 1536, and interior conductive coil (see coil 735 of FIG. 7) serving as heating agent. The side openings 1533 allow THC liquid to be absorbed. The secondary conductors make contact with the copper-plated tertiary contact 1536 that is mated with the coil. In another implementation, the entire tertiary conductor 1530 can be composed of copper.

Referring to FIG. 16a, a bottom perspective view shows a single tertiary conduction airway 1630 installed into a separative wax/oil holder 1655 in accordance with an embodiment of the present disclosure. The current view indicates structural associations provided by first and second steps in an exemplary manufacturing process of the second system, or airflow assembly. A first step in this process is to simply line up the similarly sized holes on both the airflow consolidator 1660 and the separative wax/oil holder 1655. The large threaded base holes of the airflow consolidator 1660 and bottom openings 1658 of the wax/oil holder 1655 are lined up so that the first tertiary conduction airway 1630 can install into both components easily and properly. The tertiary conductors 1630 each have a circumferential lower protrusion 1634 and run through the melted wax holder's bottom openings 1658 to connect with the airflow consolidator's base holes via the threaded portions found on each component. This connection mates the melted wax holder and airflow consolidator 1660 together in a secure manner that prevents wax migration into or out of the airflow assembly, also isolating a substantial portion of each tertiary conductor 1630 within each compartment of the melted wax/oil holder. The tertiary conductors' lower protrusions 1634 each have a diameter exceeding that of each of the melted wax holder's bottom openings 1658, thus securing each tertiary conductor against the bottom of the melted wax holder once installed. The base portion of the airflow consolidator 1660 covers and seals the melted wax holder's top openings in this mated/secured configuration, while the side openings of each tertiary conductor 1630 are isolated with the melted wax in its corresponding melted wax holder compartment. Once one tertiary conduction airway 1630 is screwed in correctly, the other two are easily installed. The current view highlights how the circumferential lower protrusion 1634 of the installed tertiary conduction airway 1630 fully closes off the bottom opening 1658 of the wax/oil holder 1655. This design ensures that no wax seeps through the second system, instead being fully retained for vaporization.

Referring to FIG. 16b, a bottom perspective view shows a nearly complete second system with fully installed components in accordance with an embodiment of the present disclosure. The finished aspect is shown with the three installed tertiary conduction airways 1630, along with the airflow consolidator 1660 and mated wax/oil holder 1655. This installation represents a third step in an exemplary manufacturing process. Once the three tertiary conduction airways 1630 are installed, the airflow consolidator 1660 and wax/oil holder 1655 are secured and sealed together. The above components now form one complete piece that is ready for installation into the supportive multi-system housing.

Figure 17:
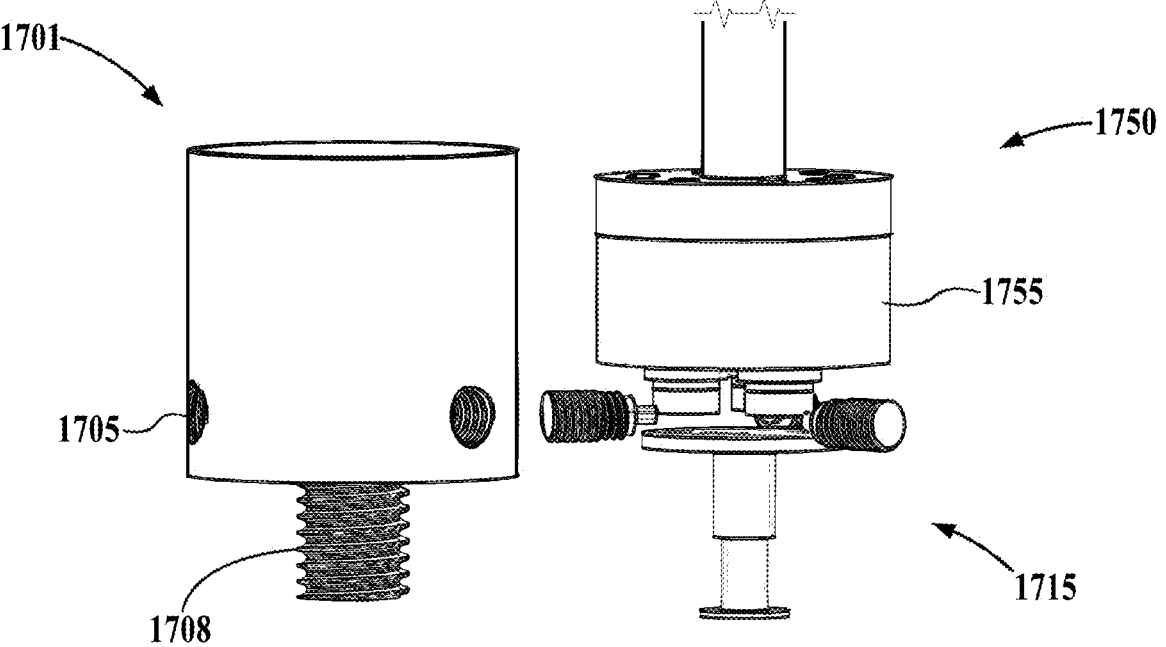
FIG. 17 illustrates a side perspective view of nearly complete first and second systems and supportive multisystem housing in accordance with an embodiment of the present disclosure.

Referring to FIG. 17, a side perspective view shows nearly complete first and second systems and supportive multi-system housing 1701 in accordance with an embodiment of the present disclosure. Depicted components are fully installed into both system one 1715 and system two 1750. As well, the view shows the supportive multi-system housing 1701 that holds both systems together. Both systems in this embodiment are shown at the proper relative height to be placed within the housing 1701. This view highlights the empty housing 1701, with threaded lower portion, or exterior port threading 1708 (of the internal port receiving the prime conductor), for screwing into a battery, along with threaded housing openings 1705 into which the secondary conductors are installed. An exemplary housing has a metallic composition. In one example of manufacturing, a strong glue is used to hold the position of the wax/oil holder 1755 within the housing 1701, at surfaces where contact is made between the two components. This represents a fourth step in an exemplary manufacturing process.

Figures 18, 19:
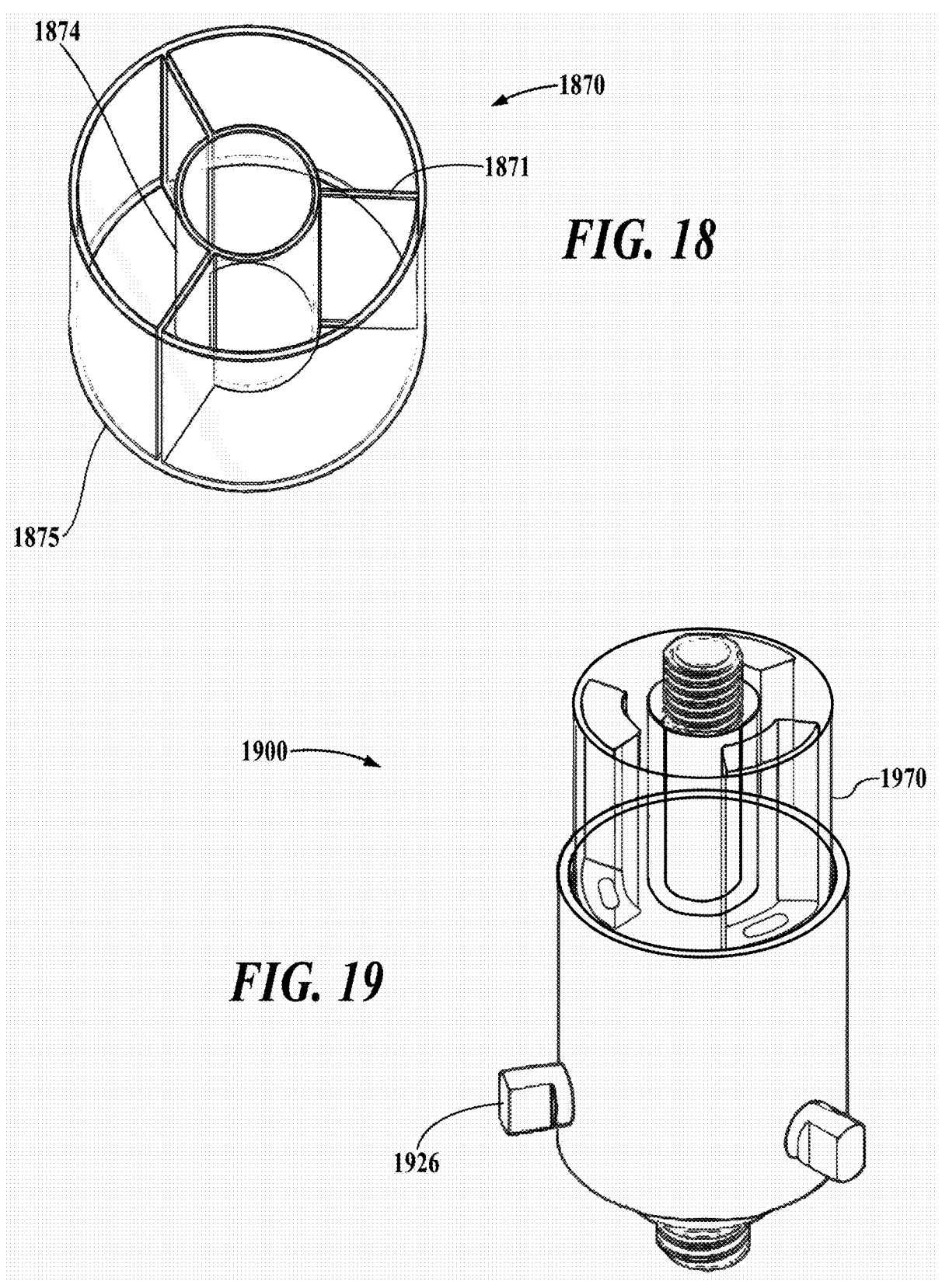
FIG. 18 illustrates a top perspective view of a strain container in accordance with an embodiment of the present disclosure.
FIG. 19 illustrates a top perspective view of an alternate embodiment of a vaping device with both a strain container and turnable knob-style user-controlled portions installed onto the vaping device in accordance with an embodiment of the present disclosure.

Referring to FIG. 18, a top perspective view shows a strain container 1870 in accordance with an embodiment of the present disclosure. The inner cylinder 1874 and outer cylinder 1875 are preferably composed of glass, while the three middle strain dividers 1871 are preferably composed of plastic, though again, a heat-certified plastic is considered. The container's design prevents any undesired mixing of wax, or contamination between strains. The inner cylinder 1874 is hollow and well-suited to receive the consolidated airway of the airflow consolidator. The strain container 1870 is placed on top of the airflow consolidator, with the bottom edges of the strain dividers 1871 being placed onto the gaps in the aforementioned layout of small holes or wax pathways. The strain container 1870 has at least three strain dividers 1871 for isolating varying substance strains. This structural partition ensures that each strain maintains its integrity and does not get improperly mixed with other strains. Placing the strain container 1870 onto the airflow consolidator is a fifth step in an exemplary manufacturing process. Additionally in that step, the three different THC strains are placed into their respective isolated strain chambers.

Referring to FIG. 19, a top perspective view shows an alternate embodiment of a vaping device 1900 featuring both a strain container 1970 and turnable knob-style user-controlled portions 1926 installed onto a vaping device in accordance with an embodiment of the present disclosure. This embodiment provides an ergonomic knob-style user-controlled portions 1926, which can be turned toward and away from the device 1900 to accomplish the same function of single-strain activation and deactivation, respectively, described above.

Figure 20:
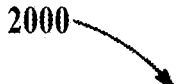
FIG. 20 illustrates a bottom perspective view of an alternate embodiment of a first system fully installed in a vaping device in accordance with an embodiment of the present disclosure.
Figure 20:
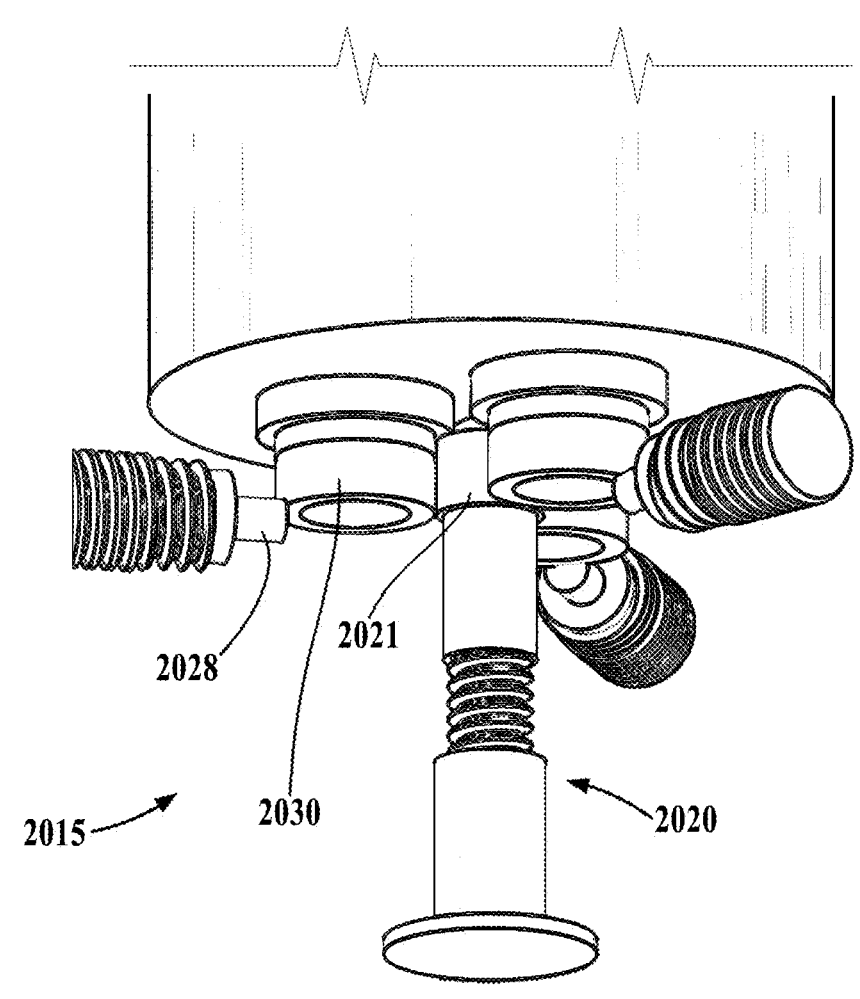

Referring to FIG. 20, a bottom perspective view shows an alternate embodiment of a first system 2015 fully installed in a vaping device 2000 in accordance with the present disclosure. This embodiment includes a non-movable prime conductor 2020 having a terminal 2021 positioned at its proximal end and in-between all three tertiary conductors 2030. Because of how the tertiary conductors 2030 are designed in this electrical system, this terminal 2021 serves as the negative in this electrical circuit. The three substance-specific secondary conductors 2028 act as the positive, and only create vapor for each of their loops; a physically contacted (i.e. by tertiary conductor 2030) secondary conductor allows current to flow.

Figure 21:
FIG. 21 illustrates a cross-sectional view of interior components of an alternate embodiment of a first system integrated with other systems in a vaping device in accordance with an embodiment of the present disclosure.
Figure 21:
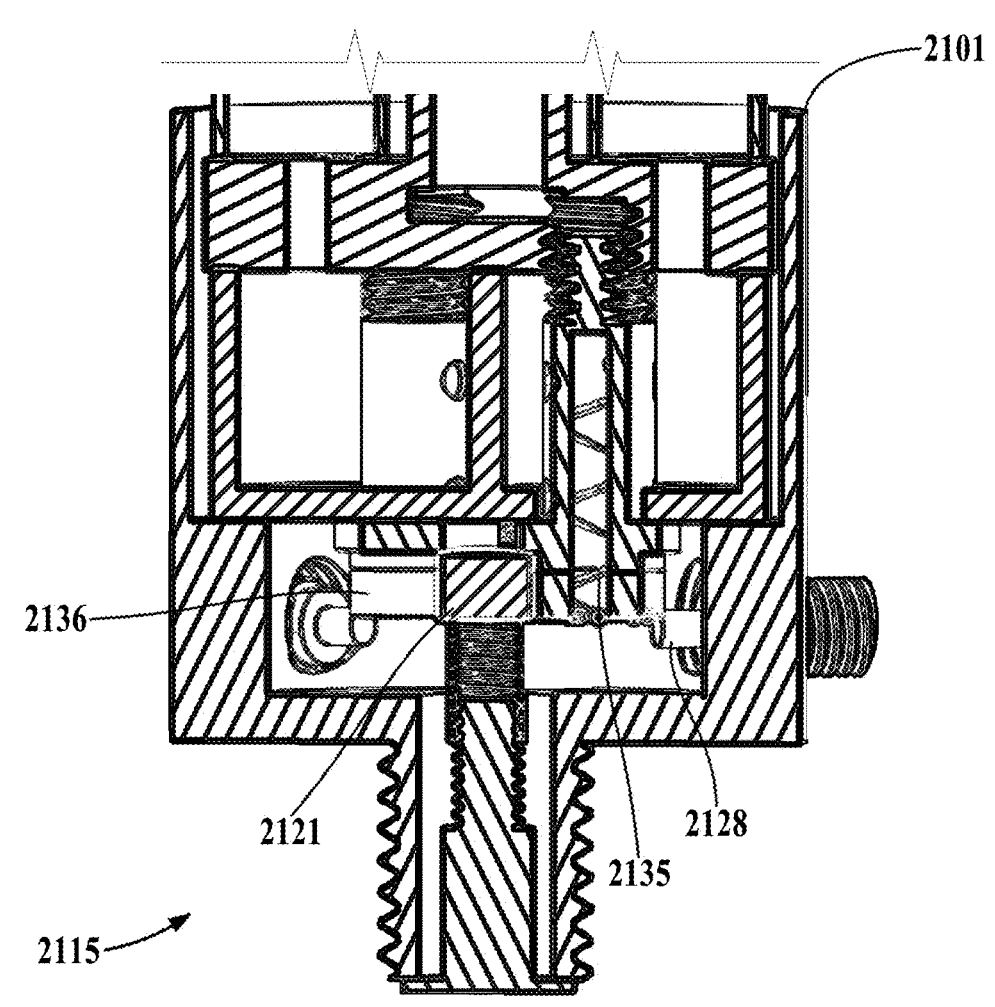

Referring to FIG. 21, a cross-sectional view shows interior components of an alternate embodiment of a first system 2115 integrated with other systems in a vaping device 2100 in accordance with an embodiment of the present disclosure. Both the anode and cathode of the heating agent (coil 2135) are touching the copper conduction portion of the tertiary contact 2136, one side touching the terminal component 2121—this serves as the negative, with the three secondary conductors 2128 acting as the positive, completing the flow back to the battery. As long as the secondary conductor 2128 is touching the coil 2135 and metal housing 2101, the electrical circuit flow will not be interrupted, and will flow back to the battery.

Figure 22:
FIG. 22 illustrates a closeup perspective cross-sectional view of interior components of an alternate embodiment of a first system integrated with other systems in a vaping device in accordance with an embodiment of the present disclosure.
Figure 22:
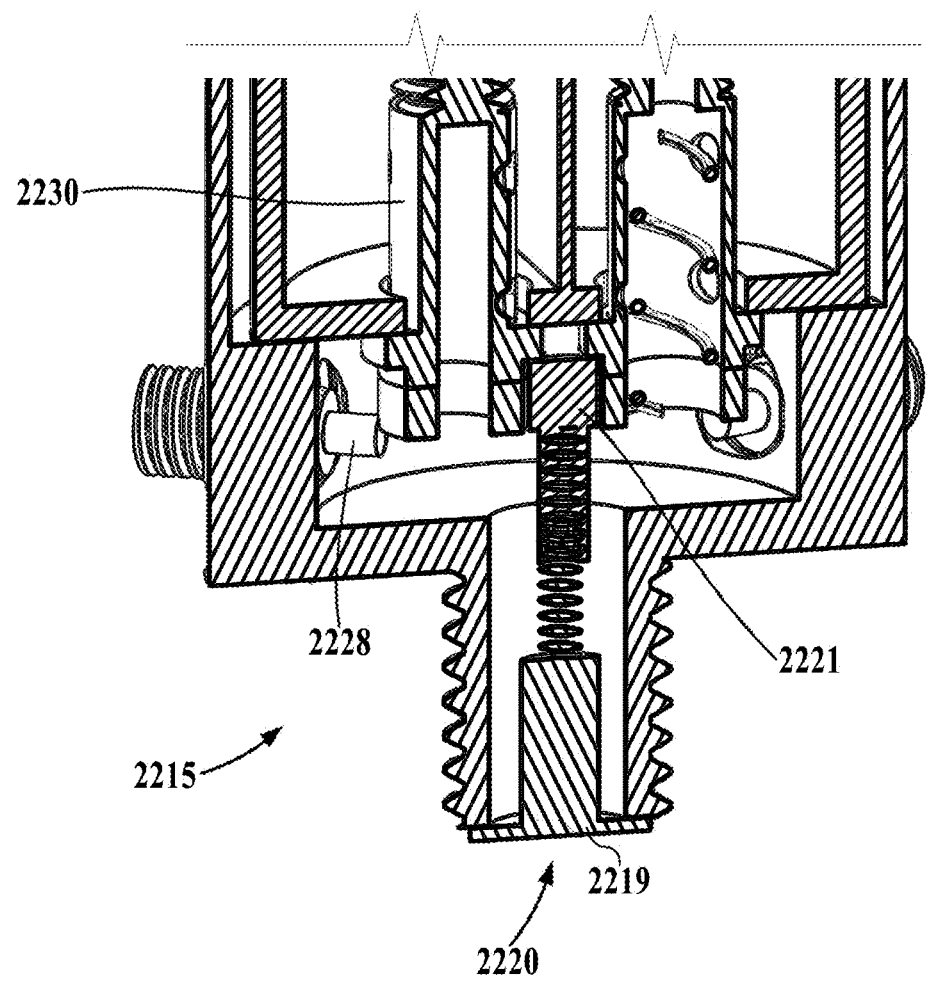

Referring to FIG. 22, a closeup perspective cross-sectional view shows interior components of an alternate embodiment of a first system 2215 integrated with other systems in a vaping device 2200 in accordance with an embodiment of the present disclosure. In the present embodiment, the non-movable prime conductor 2220 does not move up and down, but is fixed. The bottom portion of the prime conductor, or battery contactor 2219, is inserted or screwed into the prime conductor and fixed into that position. One part of the heating agent, or tertiary conductor 2230 makes contact with the negative terminal 2221 while the secondary conductors 2228 act as the positive terminals, and electrical flow is established.

Figure 23:
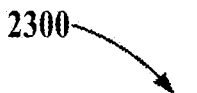
FIG. 23 illustrates a top perspective view of an alternate embodiment of a vaping device with thicker housing, covered pushbutton-style user-controlled portions, singular elongated melted wax pathways per more discrete strain chamber, and airflow release cap with modified shape in accordance with an embodiment of the present disclosure.
Figure 23:
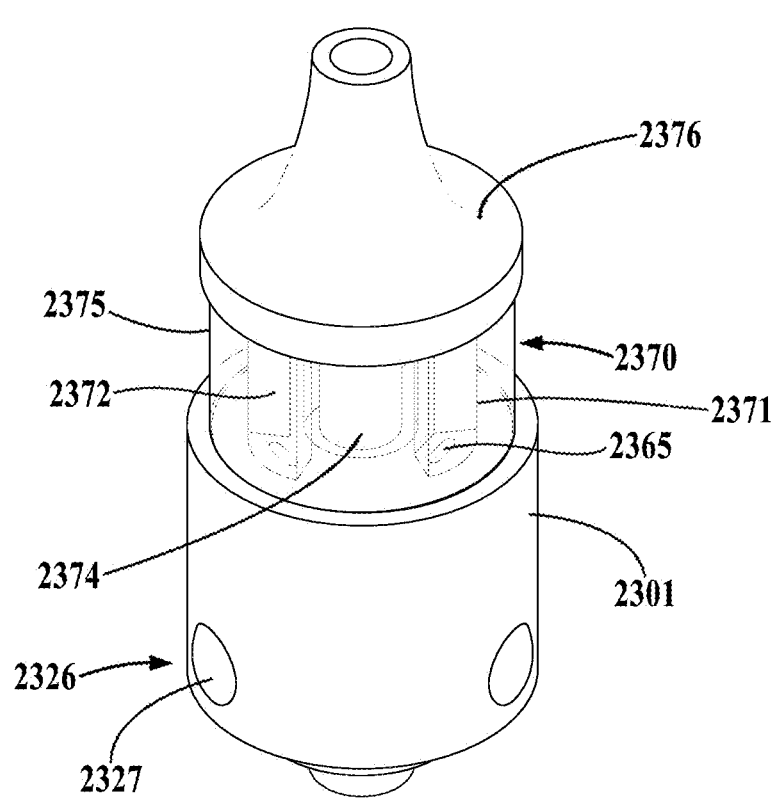

Referring to FIG. 23, a top perspective view shows an alternate embodiment of a vaping device 2300 with thicker housing 2301, covered pushbutton-style user-controlled portions 2326, singular elongated melted wax pathways 2365 of the airflow consolidator per more discrete strain chamber 2372, and airflow release cap 2376 with modified shape in accordance with an embodiment of the present disclosure. The current view shows a protective airflow release cap 2376 that is screwed on to the airflow consolidator at its threaded top opening. This component creates a system-protective ceiling over the plurality of strains so that no strains get mixed, while also ensuring that the strain container 2370 holding the wax stays in place and does not move. As well, the cap 2376 connects the airflow system so that the user can easily enjoy their vapor. Installing the protective airflow release cap 2376 is a sixth step in an exemplary manufacturing process. In some embodiments, a seventh or final manufacturing step is installing the substance activators into the housing 2301 of the device 2300.

Each smaller, more discrete strain chamber 2372 possesses a plurality of at least 2 strain dividers 2371, none of which are making contact with either the inner cylinder 2374 or outer cylinder 2375, neither are the dividers extending to or from either of the cylinders. Rather, the strain dividers 2371 forming each strain chamber 2372 are self-standing when connected edge-to-edge with each other, forming a chamber 2372 that extends upwardly away from the floor of the strain container 2370 and toward the airflow release cap 2376. Thus provided in this embodiment are smaller chambers 2372, each housing an exemplary fraction of a gram of a substance. There are ideally three discrete strain chambers 2372 in exemplary embodiments of the vaping device 2300.

The substance activators in this embodiment utilize user-controlled portions 2326 each having dual-state pushbutton (see user-controlled portion 2526 of FIG. 25) functionality and ideally being covered by a rubber pushbutton covering 2327. The pushbutton coverings 2327 provide added ergonomic benefits for the user, while offering added protection for the underlying pushbutton, especially during transport. The more streamlined shape provided by the pushbutton coverings 2327 help to prevent situations where the device 2300 gets jammed in a user's pocket, or pokes the user in the leg. Thus the device 2300 has generally smoother and sleeker contours. Further, the present embodiment eases activation of different strains or substances for users having longer fingernails, or impaired tactility such as that which occurs with arthritis or conditions that cause shaking. Additionally, each pushbutton covering 2327 can have a distinct visual indicator, including coloration, each color indicating to the user which flavor or strain is associated with each covering 2327. A metal ring surrounding the covering 2327 can help secure it onto the housing 2301 in a flush manner. An alternative manufacturing method may include glue to connect the covering 2327 with the underlying pushbutton, although the covering and underlying pushbutton do not necessarily require a direct connection or other structural association. Activation/deactivation of strains or combinations of strains, or the opening and closing of electrical circuits remains the same in this embodiment as with previously mentioned embodiments. A pressed/depressed pushbutton covering 2327 with active/closed associated circuit can further be provided with an LED light positioned inside of the covering that can illuminate the activated user-controlled portion 2326 and covering, thereby providing visual confirmation to the user that they've correctly activated a desired strain, while inactive strains remain non-illuminated. This can be accomplished by lining up the LED in the electrical path with its associated pushbutton/substance activator. A less obvious sign of button activation could be felt as a result of button depression. Pressing the pushbutton once again raises it back into the off position, opening the electrical circuit and deactivating the associated strain. In some examples, the user may see a visual indication of the depression/raising of the pushbutton or covering 2327.

Referring to FIG. 24, a closeup perspective cross-sectional view shows an alternate embodiment of a substance activator 2425 being inserted through an unthreaded housing opening 2405 and having a pushbutton style user-controlled portion 2426 in accordance with an embodiment of the present disclosure. The pushbutton style user-controlled portion 2426 can have an angular shape (i.e. substantially cubic) or a more circular shape and contour (see user-controlled portion 2526 of FIG. 25). Either shape may optionally have a slot running through it centrally and orthogonally relative to the length of the substance activator, which has the secondary conductor 2428 proximally positioned at one end, and the pushbutton style user-controlled portion 2426 distally positioned at the opposing end, as illustrated in the drawing. A line of explosion indicates the path of installation for the substance activator 2425 through the housing opening 2405 and into the interior of the housing 2401, reaching a final position wherein the secondary conductor 2428 remains in static conductive contact with its associated tertiary conductor 2430, such that it is a non-movable component in this embodiment, regardless of pushbutton activation. Thus, in this unchanging position, the secondary conductor 2428 maintains an electrically conductive association with its contacted tertiary conductor 2430. In this embodiment, an exemplary secondary conductor 2428 is threaded, and mates with one of at least three threaded frame holes 2442 of an insulative support frame 2441 to reach its final position. Each of the three secondary conductors 2428 has a corresponding insulative support frame hole 2442 found through the cylindrical insulative support frame 2441. The support frame 2441 ensures that the secondary conductors 2428 do not make contact with any surfaces of the metallic housing 2401, securing their final position and ensuring strong contact with the tertiary conductor 2430. This insulative aspect prevents contamination or corruption of the electrical circuit flow required by this alternate embodiment to function properly, without it, the circuit would remain perpetually closed and the strain always active. The conductive contact point between secondary conductor 2428 and tertiary conductor 2430 creates the initial point of electrical flow for the pushbutton style substance activator 2425. In this alternate embodiment, the metallic supportive housing 2401 serves as the negative terminal in the electrical circuit, and returns its received current back to the inserted battery—which serves as the originating, positive terminal in the electrical circuit. In most embodiments, each electrical circuit is isolated per each pair of tertiary conductor 2430 and secondary conductor 2428, along with the prime conductor.

Referring to FIG. 25, a side perspective view shows an alternate embodiment of a substance activator 2525 having a pushbutton style user-controlled portion 2526 in accordance with an embodiment of the present disclosure. Electricity must flow from within the substance activator 2525 (this current gained from the secondary conductor 2528) to a portion of its exterior that is in fixed conductive contact with the metallic supportive housing (see housing 2401 of FIG. 24), this metallic, conductive exterior portion being an intermediary pushbutton conductor 2529. Thus initiated by a pressed pushbutton, electric current gained from the tertiary conductor enters the secondary conductor 2528, and through the interior of the secondary conductor 2528 to reach the intermediary conductor 2529 and contacted housing, the electrical current returning to the battery via the housing. The only physically moving components in this process are those associated with the pushbutton style user-controlled portion 2526, and the pushbutton covering if implemented in this embodiment. Other examples may omit the pushbutton covering to only include a version of the pushbutton style user-controlled portion 2526 as described and shown in FIGS. 24 and 25. The intermediary pushbutton conductor 2529 can be a circumferential exterior band running centrally and orthogonally to the length of the substance activator 2525, such that it is positioned in-between the secondary conductor 2528 and the pushbutton style user-controlled portion 2526. In another example, the intermediary conductor 2529 can be a minimally protruding plate or small raised portion of the exterior of the substance activator 2525.

Referring to FIG. 26, a front view shows an alternate embodiment of a vaping device 2600 with thicker housing 2601, covered pushbutton-style user-controlled portions 2626, airflow release cap 2676 with modified shape, and modified lower region in accordance with an embodiment of the present disclosure. This embodiment of the cap 2676 includes a cap pathway 2677 which is more gradually tapered from the base of the cap to the maximal height of the cap pathway, or its distal end with an opening, the circumferential portion surrounding the opening not protruding outwardly and laterally away from the opening, but instead being the portion of the cap pathway with the smallest diameter. The modified lower region includes at least one protrusion with rounded lateral contour and flat bottom face, each protrusion extending away from the lower region of the device 2600 in a direction aligned with the vertical axis of the device, a plurality of such protrusions getting progressively smaller in diameter. In the exemplary example shown, the second and final protrusion includes a double-sided hole running laterally through the protrusion, such that the holes are connected via a tunnel 2609. This double-sided hole or tunnel 2609 assists in supporting and optimizing airflow. The tunneled portion lies above the exterior "510" port threading 2608. Flowing air enters through the tunnel 2609 and into the internal prime conductor port of the housing 2601, moving upward into the housing interior, upward through the tertiary conductors, upward through the large threaded base holes of the airflow consolidator's base portion, upward through the consolidated airway 2662, and upward through and exiting the cap pathway 2677.

Figure 27:
FIG. 27 illustrates a side perspective view of an alternate embodiment of an assembled but unhoused vaping device with a modified non-movable prime conductor, an insulation system, and turnable knob-style user-controlled portions in accordance with an embodiment of the present disclosure.
Figure 27:
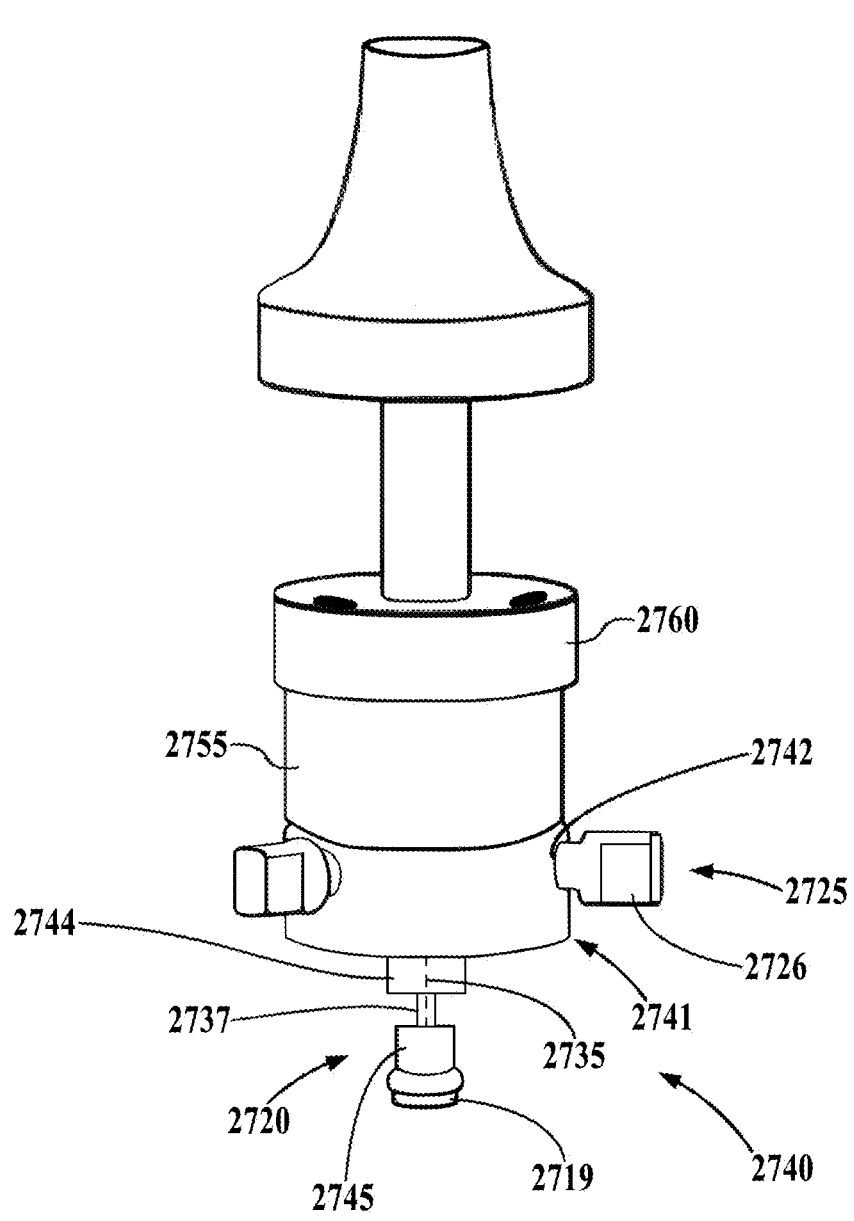

Referring to FIG. 27, a side perspective view shows an alternate embodiment of an assembled but unhoused vaping device 2700 with a modified non-movable prime conductor 2720, an insulation system 2740, and turnable knob-style user-controlled portions 2726 in accordance with an embodiment of the present disclosure. In this embodiment, in order to activate a strain of a substance, a user twists the associated knob-style user-controlled portion 2726 of a substance activator 2725 until a conductive portion of the knob makes contact with the conductive housing. This metal-on-metal contact forms a closed circuit. The electrical current received from the attached battery thus activates the associated heating agent, or tertiary conductor, that has an electrically conductive association with the secondary conductor of the substance activator 2725. The user may manipulate any combination of the knobs in this way to vape at least six strains simultaneously from the same vaping device 2700. Reopening a circuit simply requires the user to turn the knob in the reversed direction, in order to screw it off of the metallic wall so that contact is lost between user-controlled portion 2726 and the supportive housing, which can have an exemplary composition of steel, aluminum, or other highly effective conductor. In this embodiment, the tertiary conduction airways (not shown), installed with the combined separative wax/oil holder 2755 and airflow consolidator 2760, each comprise wrapped coils 2735 that extend from the tertiary conductor downward, extending past the insulative support frame 2741 and joining together in a singular wrapped or twisted portion, this portion inserting through the internal prime conductor port (see internal port 407 of FIG. 4), such that the coils become, or substantially form the modified non-movable prime conductor 2720. The prime conductor still terminates in a battery contactor 2719, as in previously mentioned examples.

An electrical insulation system 2740 prevents conductive contact between the electrical assembly and the supportive housing. The insulation system 2740 comprises an insulative support frame 2741 having support frame holes 2742 through which the substance activators 2725 are inserted, the threaded secondary contacts of the substance activators being the portion making contact with the frame holes. An exemplary insulative support frame 2741 can be composed of heat resistant plastic. The insulation system 2740 further comprises a coil restraint insulator 2744 and insulative battery contact support 2745, both of which support and protect/insulate their associated conductive portions (coil restraint 2737 and battery contactor 2719, respectively) of the modified prime conductor 2720 from other conductive elements, especially the supportive housing. An exemplary composition for both the insulative battery contact support 2745 and coil restraint insulator 2744 can be rubber. The knob-style user-controlled portions 2726 can generally be composed of aluminum in one example.

Figure 28:
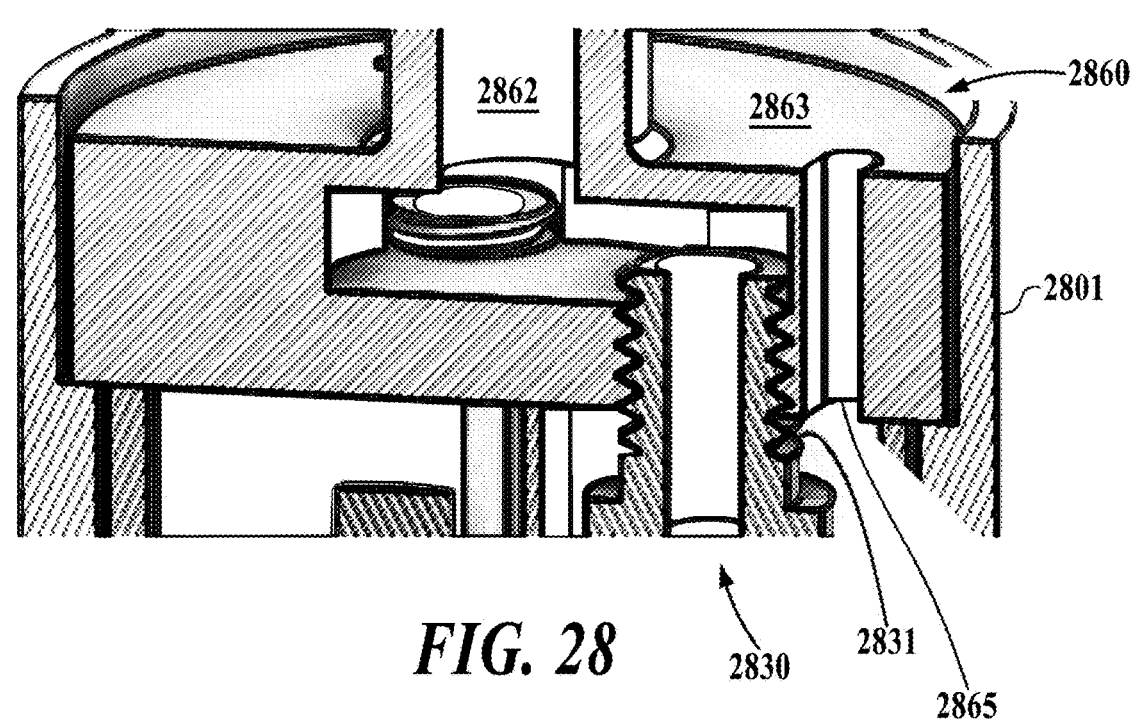
FIG. 28 illustrates a closeup perspective cross-sectional view highlighting an alternate embodiment of a melted wax pathway in accordance with an embodiment of the present disclosure.

Referring to FIG. 28, a closeup perspective cross-sectional view highlights an alternate embodiment of a melted wax pathway 2865 in accordance with an embodiment of the present disclosure. The singular elongated melted wax pathway 2865 is one of three, rather than nine, in this embodiment. Each melted wax pathway 2865 corresponds with a strain chamber (see strain chamber 2372 of FIG. 23), the pathway opening within the strain chamber to receive melted substance, wax, or oil. The illustration highlights the structural isolation provided by both the melted wax pathway 2865 and tertiary conduction airway 2830, which are positioned adjacent to each other so that the threaded top portion 2831 of the tertiary conductor terminates at an opening positioned substantially higher than the bottom opening of the melted wax pathway 2865, the tertiary conductor further being shielded (at a distance) by the ceiling of the base portion 2863 of the airflow consolidator 2860, which has no other fully-through openings other than the melted wax pathways. The melted wax migrates from a strain chamber through only its corresponding melted wax pathway 2865 into and being further isolated by only the corresponding melted wax compartment. Once in a melted wax compartment, the melted wax migrates into only the corresponding tertiary conductor 2830 via its side opening, to be burned within the tertiary conductor. The generated vapor travels through only that same tertiary conductor 2830 via its hollow body, exiting out of its open top threaded portion 2831, the vapor further traveling into the base portion 2863 of the airflow consolidator 2860, therefrom traveling into and through the consolidated airway 2862 and finally exiting from the airflow release cap. Thus, wax or oil migration through at least three melted wax pathways 2865 (into the separative wax/oil holder) and rising smoke through the tertiary conduction airways 2830 occur completely separately and in isolation, together within the confined space of the housing 2801. Moreover, the secure threaded engagement between base holes (see base holes 1364 of FIG. 13b.) of the base portion 2863 and tertiary conduction airways 2830 further blocks any upward migration of melted wax or oil from the wax holder below. In this way, the above-mentioned terminal openings found at the top portions 2831 of the tertiary conduction airways 2830 lie within an interior compartment the base portion 2863 that is devoid of any wax/oil in solid or liquid form, instead solely housing or funneling smoke/vapor upward into the consolidated airway 2862. The base portion 2863 thus structurally provides a dual function, providing a path for downward migration of a substance/wax/oil, while simultaneously providing a path for upward airflow/vapor.

Figure 29:
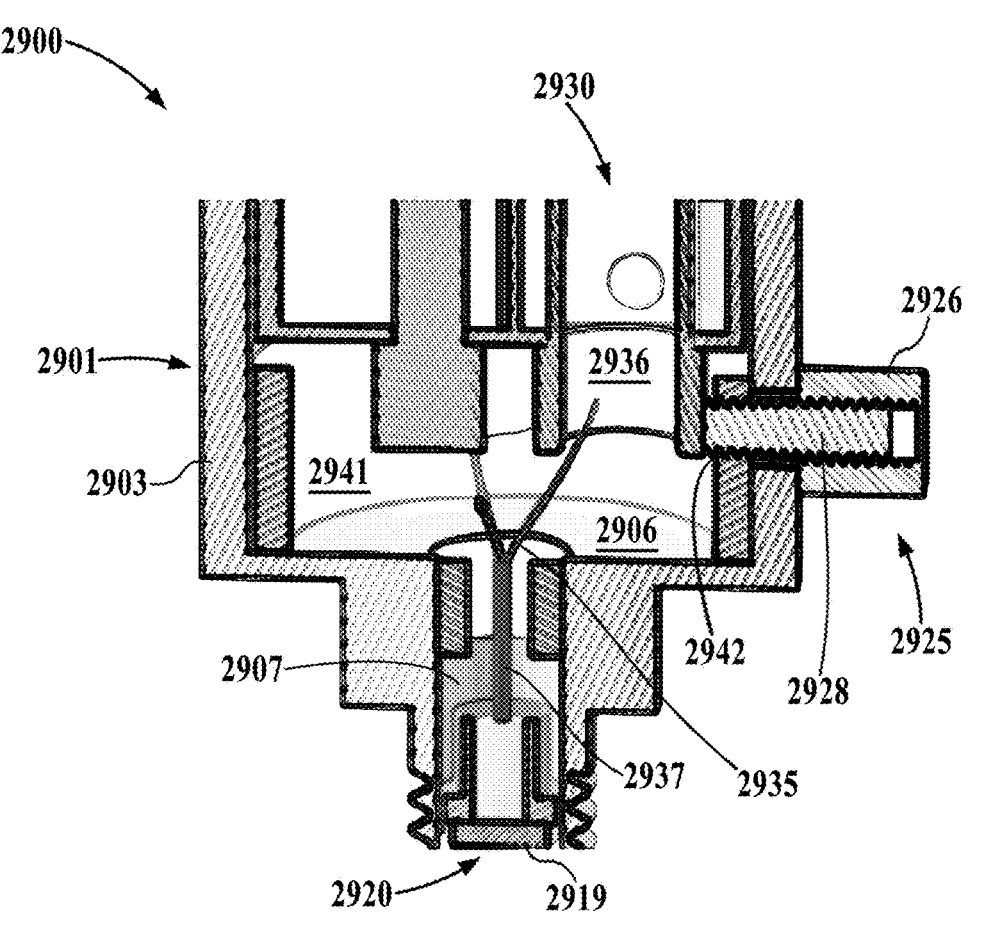
FIG. 29 illustrates a closeup perspective cross-sectional view of an alternate embodiment of a vaping device highlighting the positioning of a non-moving secondary conductor and modified non-movable prime conductor in accordance with an embodiment of the present disclosure.

Referring to FIG. 29, a closeup perspective cross-sectional view shows an alternate embodiment of a vaping device 2900 highlighting the positioning of a non-moving secondary conductor 2928 and modified non-movable prime conductor 2920 in accordance with an embodiment of the present disclosure. Once the device 2900 is screwed into a "510"-compatible battery, the battery contactor 2919 obtains conductive contact with the battery, providing a positive terminal. The battery itself can be activated to initiate electrical flow to the battery contactor 2919 and through the connected non-movable prime conductor 2920. The non-movable prime conductor 2920 includes coils 2935 that extend from each tertiary conductor 2930 and join to form a portion of the prime conductor. The joined coils 2935 are physically combined via the conductive coil restraint 2937 which circumferentially surrounds and compresses the three extended coils through a substantial portion of the internal port 2907 of the housing 2901. The coil restraint 2937 meets or terminates near the battery contactor 2919 on one end, while its contacted/combined coils 2935 separate into three portions as they exit the top of the coil restraint, each leading to one of three tertiary conductors 2930 through the tertiary contacts 2936 of the tertiary conductors. Thus, all three coils 2935 share the same positive terminal provided by the battery contactor 2919 and connected battery. The user chooses to close a circuit by manipulating its associated substance activator 2925 via user-controlled portion 2926, and electricity then flows into that circuit's connected coil 2935. Electrical energy flows from the coil 2935 to its contacted non-moving secondary conductor 2928, from there flowing into a conductive portion of the user-controlled portion 2926 that is in electrically conductive contact with the conductive supportive housing 2901. Here the housing 2901 or its exterior "510" port threading serves as the negative in the completed/closed electrical circuit.

Each exemplary threaded secondary conductor 2928 is being held in place and insulated from other conductive elements by the insulative support frame 2941. The tubular support frame 2941 is positioned on the interior of the housing 2901, having a lateral circumferential surface contacting an interior surface of the thick first wall 2903, and a bottom circumferential surface contacting the interior housing floor 2906. The support frame 2941 ensures that each secondary conductor 2928 is properly positioned and lined up with its contacted tertiary conductor 2930 for optimal conductivity. Each exemplary support frame hole 2942 is threaded to circumferentially support its inserted secondary conductor 2928 into the fixed position. In this embodiment, only movement of the user-controlled portion 2926, toward and away from the housing 2901, is required to close and open the circuit, respectively. An optional manufacturing step may include adding sealant to the secondary conductor 2928 for added structural support.

Figure 30:
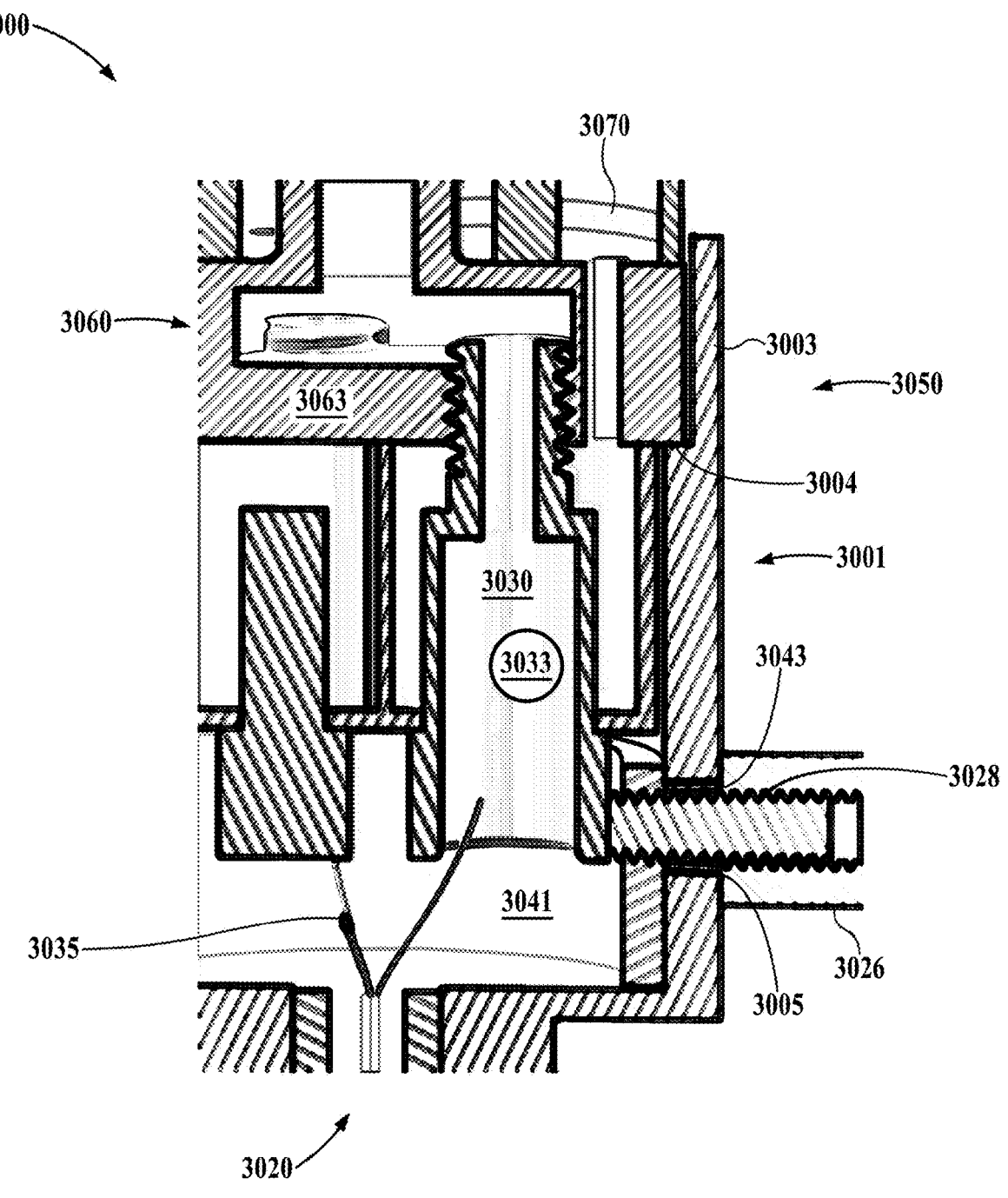
FIG. 30 illustrates a closeup perspective cross-sectional view of an alternate embodiment of a vaping device highlighting the relationship between housing and interior components, as well as a tertiary conduction airway with single side body opening and extended coils which structurally and conductively integrate with a modified non-movable prime conductor in accordance with an embodiment of the present disclosure.

Referring to FIG. 30, a closeup perspective cross-sectional view shows an alternate embodiment of a vaping device 3000 highlighting the relationship between housing and interior components, as well as a tertiary conduction airway 3030 with body having a single side opening 3033 and extended coils 3035 which structurally and conductively integrate with a modified non-movable prime conductor 3020 in accordance with an embodiment of the present disclosure. In most embodiments, each tertiary conductor 3030 corresponds with a strain chamber, a threaded base hole, a melted wax pathway, a melted wax holder compartment and bottom opening, and a secondary conductor 3028. In this embodiment, the thick first wall 3003 of the housing 3001 still supports the airflow assembly 3050 via the interior housing ledge 3004. However, in this embodiment, the interior housing ledge 3004 makes contact with the base portion 3063 of the airflow consolidator 3060. The ledge 3004 further supports the weight of the strain container 3070 and airflow release cap positioned above all systems.

In the current depiction, the user-controlled portion 3026 is turned toward the housing 3001 to conductively contact it and close the circuit for the associated substance/strain. In one example, the user-controlled portion 3026 has a limited range of travel along the secondary conductor 3028, such that rotating it away from this housing-contacted position and away from the vaping device 3000 does not result in detachment of the user-controlled portion from the device. In some examples, in addition to being secured/insulated by an insulative support frame 3041, each secondary conductor 3028 can further be insulated from its corresponding housing opening 3005 by being threaded through an insulative support tube 3043. Each insulative support tube 3043 has an inner circumferential surface contacting the secondary conductor 3028 and an exterior circumferential surface contacting the housing opening 3005, the tube 3043 further having a length corresponding to the depth of the housing opening, the tube 3043 insertable through the housing opening and the secondary conductor insertable through the support tube. In yet other examples, the plurality of insulative support tubes 3043 are sufficient enough on their own to secure and insulate the secondary conductors 3028; in such embodiments, an insulative support frame 3041 may not be needed.

Figure 31:
FIG. 31 illustrates a closeup perspective view of an alternate embodiment of a vaping device highlighting microchip usage for battery optimization and other tasks in accordance with an embodiment of the present disclosure.
Figure 31:
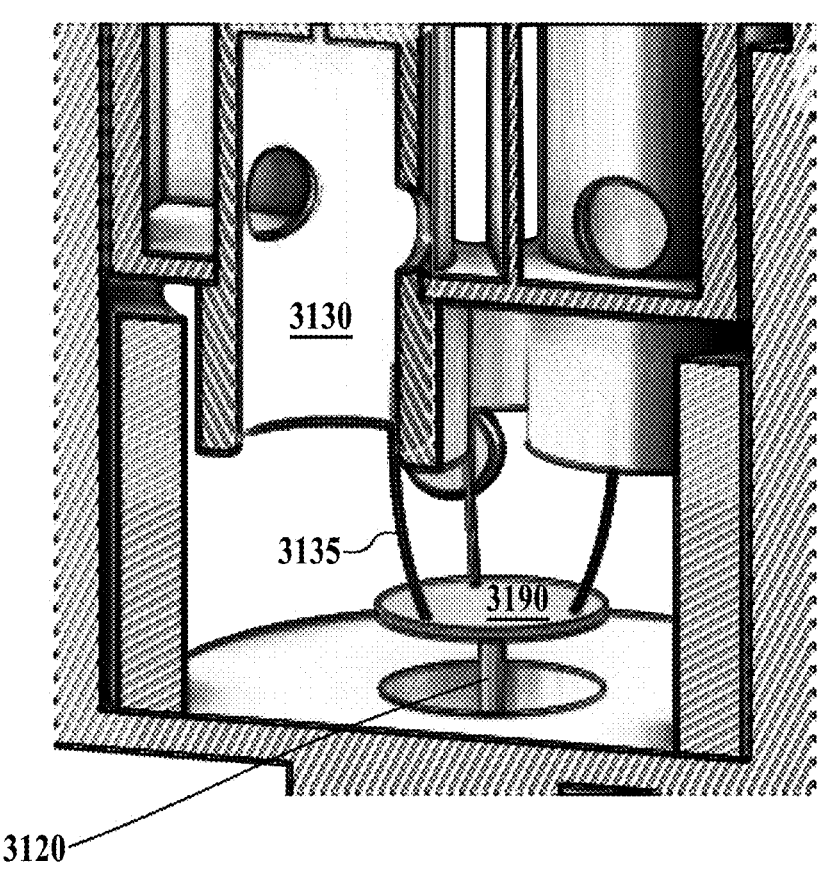

Referring to FIG. 31, a closeup perspective view shows an alternate embodiment of a vaping device 3100 highlighting usage of a microchip 3190 for battery optimization and other tasks in accordance with the present disclosure. The exemplary microchip 3190 is physically integrated with the non-movable prime conductor 3120, having a structural association with the extended coils 3135, and having a communicative electrical association with the connected battery. The microchip runs at least one program that can activate and deactivate each heating agent or tertiary conductor 3130 individually or in combination at a substantially accelerated rate. The rapid on/off activity provided by the microchip optimizes battery utilization in order to provide a programmed means for producing at least seven strains to be vaped.

Many variations may be made to the embodiments described herein. All variations are intended to be included within the scope of this disclosure. The description of the embodiments herein can be practiced in many ways. Any terminology used herein should not be construed as restricting the features or aspects of the disclosed subject matter. The scope should instead be construed in accordance with the appended claims.

There may be many other ways to implement the disclosed embodiments. Various functions and elements described herein may be partitioned differently from those shown without departing from the scope of the disclosed embodiments. Various modifications to these implementations may be readily apparent to those skilled in the art, and generic principles defined herein may be applied to other implementations. Thus, many changes and modifications may be made to the disclosed embodiments, by one having ordinary skill in the art, without departing from the scope of the disclosed embodiments. For instance, different numbers of a given element or module may be employed, a different type or types of a given element or module may be employed, a given element or module may be added, or a given element or module may be omitted.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The invention claimed is:

1. A vaping device that enables a user to simultaneously vape a plurality of substance strains, the device comprising:

(a) a strain container further comprising an outer cylinder, an inner cylinder, and at least three isolated strain chambers positioned between the outer and inner cylinders, each chamber configured to hold an individual strain as a solid wax;

(b) a first system including an electrical assembly, the electrical assembly further comprising:

i. a prime conductor having a battery contactor;

ii. at least three substance activators, each further comprising a secondary conductor and user-controlled portion;

iii. at least three tertiary conductors, each further comprising a conductive coil, a tertiary contact, and a hollow body, the hollow body having a threaded top opening and at least one side opening, the hollow body housing the coil, the coil serving as a heating agent;

iv. an insulation system;

wherein the electrical assembly is configured to melt the solid wax, the melted wax being vaporized within each hollow body of a tertiary conductor;

(c) a second system including an airflow assembly, the airflow assembly further comprising:

i. a melted wax holder having at least three bottom openings, at least three larger opposing top openings, and at least three separative walls, the walls forming at least three compartments for receiving melted wax;

ii. an airflow consolidator further comprising a consolidated airway and a base portion, the consolidated airway having a threaded top opening, the base portion having at least three threaded base holes and at least three melted wax pathways, the threaded base holes running partially through the base portion, the melted wax pathways running fully through the base portion, each pathway leading from a strain chamber to a wax holder compartment, the inner cylinder of the strain container receiving the consolidated airway;

iii. an airflow release cap having a threaded cap pathway;

wherein the airflow assembly is configured to isolate the melted wax;

(d) a supportive housing for components in the first and second systems, the supportive housing further comprising a first wall having a first wall thickness, a second wall having a second wall thickness, wherein the first wall thickness is greater than the second wall thickness, an interior floor, and an internal port, the first wall having at least three openings running through it, both first and second walls each having a circumferential interior surface, the interior surface of the first wall extending orthogonally away from the interior floor and terminating in an interior ledge, the interior surface of the second wall extending orthogonally away from said ledge, the internal port having an exterior with standard threading for accepting a battery; and wherein the substance activators are installed through the supportive housing openings, wherein the insulation system prevents conductive contact between the electrical assembly and the supportive housing, wherein each tertiary conductor corresponds with a strain chamber, a threaded base hole, a melted wax pathway, a melted wax holder compartment and bottom opening, and a secondary conductor, wherein the internal port receives the prime conductor, a connected battery providing electrical current to the prime, secondary, and tertiary conductors via the battery contactor, wherein each paired secondary and tertiary conductor are configured to form an isolated electrical circuit with the prime conductor, the user-controlled portions being manipulatable to close and open each circuit, wherein a closed circuit results in the vaporization of only the corresponding strain, wherein the isolated strains can be vaped individually or in any combination simultaneously, the second system configured to consolidate the combined vapors into a single airflow to be vaped, and wherein the combination vaping produces at least six strains.

2. The vaping device of claim 1, wherein the tertiary conductors each have a circumferential lower protrusion and run through the melted wax holder's bottom openings to connect with the airflow consolidator's base holes via the threaded portions, said connection mating components of the airflow assembly together in a secure manner and preventing wax migration into or out of the assembly, the tertiary conductors' lower protrusions each having a diameter exceeding that of each of the melted wax holder's bottom openings, the airflow consolidator's base portion covering and sealing the melted wax holder's top openings, the side opening(s) of each tertiary conductor being isolated with the melted wax in the corresponding melted wax holder compartment, wherein each conductive coil generates heat when its electrical circuit is closed, the heat melting and vaporizing only the wax in the corresponding strain chamber, the melted wax migrating therefrom through only the corresponding melted wax pathway into and being further isolated by only the corresponding melted wax compartment, the melted wax migrating therefrom into only the corresponding tertiary conductor via its side opening(s), the generated vapor traveling through only the corresponding tertiary conductor via its hollow body and exiting out of its top threaded opening, the vapor further traveling into the base portion of the airflow consolidator, therefrom traveling into and through the consolidated airway and finally exiting from the airflow release cap.

3. The vaping device of claim 2, wherein the prime and secondary conductors are movable, wherein the prime conductor further comprises a main hot plate, wherein a closed electrical circuit is formed by positioning the main hot plate into conductive contact with a substance activator that has been manipulated by the user to be in conductive contact with its corresponding tertiary conductor, wherein battery installation pushes the prime conductor so that the main hot plate is positioned into said conductive contact, wherein the interior housing ledge supports the airflow assembly and makes contact with the melted wax holder, wherein the strain container's strain chambers are each formed by at least two strain dividers, and wherein the substance activators include active substance indicators configured to visually inform the user that an electrical circuit has been opened or closed, each active substance indicator having a distinct coloration.

4. The vaping device of claim 2, wherein the prime and secondary conductors are non-movable, wherein the secondary and tertiary conductors are in fixed conductive contact, and wherein the thick first wall of the housing supports the airflow assembly via the interior housing ledge.

5. The vaping device of claim 4, wherein the coils extend from each tertiary conductor and join to form a portion of the prime conductor, the joined coils conductively covered with a coil restraint, wherein the insulation system further comprises an insulative support frame, a coil restraint insulator, and an insulative battery contact support, the insulative support frame positioned upon the interior housing floor and circumferentially contacting the interior surface of the thick first wall, the support frame having at least three holes running through it to receive the secondary conductors, and wherein the interior housing ledge makes contact with the base portion of the airflow consolidator.

6. The vaping device of claim 4, wherein the user-controlled portions are a turnable knob-style, a conductive portion of the user-controlled portion making contact with the supportive housing to close the corresponding electrical circuit when the knob is fully turned toward the housing.

7. The vaping device of claim 4, wherein the user-controlled portions are dual-state pushbuttons, the substance activator further comprising an external intermediary conductor in fixed conductive contact with the supportive housing, the substance activator configured to close the corresponding circuit once the pushbutton is pressed, and open said circuit when the pushbutton is pressed again.

8. The vaping device of claim 7, wherein the pushbuttons include rubber coverings, each rubber covering having a distinct visual indicator via coloration or LED light, and wherein the pressed pushbutton conductively links the secondary conductor, intermediary conductor, and housing, the electrical current returning to the battery via the housing.

9. The vaping device of claim 4, wherein the vaping device includes a microchip to provide a programmed means for vaping at least seven strains, and wherein the user-controlled portions are enhanced with LED lights.

10. A vaping device that enables a user to simultaneously vape a plurality of substances, the device comprising:
    (a) a strain container further comprising at least three isolated strain chambers, each chamber configured to hold an individual strain of a substance in liquid or solid form;
    (b) a first system including an electrical assembly, the electrical assembly configured to activate at least three heating agents, each heating agent corresponding with a strain chamber, each heating agent configured to vaporize its corresponding strain;
    (c) a second system including an airflow assembly, the airflow assembly configured to further isolate the strains in liquid form while providing pathways of travel for the vapors;
    (d) a conductive housing for components in the first and second systems; and
    wherein the isolated strains can be vaped individually or in any combination simultaneously, the second system configured to consolidate the combined vapors into a single airflow to be vaped, and
    wherein the combination vaping produces at least six strains; wherein the strain container further comprises an outer cylinder and an inner cylinder, the strain chambers positioned between the cylinders, wherein the electrical assembly further comprises a prime conductor, at least three substance activators, and at least three tertiary conductors, and wherein the airflow assembly further comprises a liquid substance holder and an airflow consolidator.

11. The vaping device of claim 10, wherein each substance activator further comprises a secondary conductor and user-controlled portion, and wherein each tertiary conductor further comprises a conductive coil and a hollow body that houses the coil, the coil serving as the heating agent.

12. The vaping device of claim 11, wherein the liquid substance holder further comprises at least three isolated compartments for receiving liquid substance, and wherein the airflow consolidator further comprises a consolidated airway and a base portion, the base portion having at least three base holes and at least three liquid substance pathways, the base holes running partially through the base portion, the liquid substance pathways running fully through the base portion, each pathway leading from a strain chamber to a liquid substance holder compartment, the inner cylinder of the strain container receiving the consolidated airway.

13. The vaping device of claim 12, wherein each tertiary conductor corresponds with a strain chamber, a liquid substance pathway, a liquid substance holder compartment, and a secondary conductor, wherein each paired secondary and tertiary conductor are configured to form an isolated electrical circuit with the prime conductor, the user-controlled portions being manipulatable to close and open each circuit, wherein a closed-circuit results in the vaporization of only the corresponding substance.

14. The vaping device of claim 13, wherein the tertiary conductors, liquid substance holder, and airflow consolidator are configured to securely mate together such that liquid substance cannot migrate out of the liquid substance holder, nor can liquid substance enter the holder except through the liquid substance pathways, wherein liquid substance produced from a closed circuit migrates from the corresponding strain chamber to the corresponding liquid substance holder compartment, therefrom migrating into the hollow body of the corresponding tertiary conductor, the hollow body serving as an airway for the vaporized substance, wherein the vapor exits the tertiary conductor and enters the base portion followed by the consolidated airway of the airflow consolidator.

15. The vaping device of claim 14, wherein the prime and secondary conductors are non-movable, and wherein the secondary and tertiary conductors are in fixed conductive contact.

16. The vaping device of claim 15, wherein the user-controlled portions are a turnable knob-style, a conductive portion of the user-controlled portion making contact with the conductive housing to close the corresponding electrical circuit when the knob is fully turned toward the housing.

17. The vaping device of claim 15, wherein the user-controlled portions are dual-state pushbuttons, the substance activator configured to close the corresponding circuit once the pushbutton is pressed, and open said circuit when the pushbutton is pressed again.

18. The vaping device of claim 17, wherein the pushbuttons include coverings, each covering having a distinct visual indicator.

19. The vaping device of claim 15, wherein the vaping device includes a microchip to provide a programmed means for vaping at least seven strains.

* * * * *